United States Patent
Rao et al.

(10) Patent No.: US 10,208,058 B2
(45) Date of Patent: Feb. 19, 2019

(54) PROCESS FOR THE PREPARATION OF MACROCYCLIC KETONE ANALOGS OF HALICHONDRIN B OR PHARMACEUTICALLY ACCEPTABLE SALTS AND INTERMEDIATES THEREOF

(71) Applicant: CIPLA LIMITED, Mumbai (IN)

(72) Inventors: Dharmaraj Ramachandra Rao, Thane (IN); Geena Malhotra, Mumbai (IN); Venkata Srinivas Pullela, Bangalore (IN); Vinod Parameshwaran Acharya, New Panvel (East) (IN); Nagarjuna Reddy Vantadou, Kharghar (IN)

(73) Assignee: CIPLA LIMITED, Mumbai (IN)

( * ) Notice: Subject to any disclaimer, the term of this patent is extended or adjusted under 35 U.S.C. 154(b) by 0 days.

(21) Appl. No.: 15/510,077

(22) PCT Filed: Sep. 9, 2015

(86) PCT No.: PCT/IN2015/000354
§ 371 (c)(1),
(2) Date: Mar. 9, 2017

(87) PCT Pub. No.: WO2016/038624
PCT Pub. Date: Mar. 17, 2016

(65) Prior Publication Data
US 2017/0240561 A1    Aug. 24, 2017

(30) Foreign Application Priority Data
Sep. 9, 2014 (IN) .......................... 2869/MUM/2014

(51) Int. Cl.
| | | |
|---|---|---|
| C07D 407/14 | (2006.01) |
| C07D 493/22 | (2006.01) |
| C07F 7/18 | (2006.01) |
| C07D 519/00 | (2006.01) |

(52) U.S. Cl.
CPC .......... *C07D 493/22* (2013.01); *C07D 407/14* (2013.01); *C07D 519/00* (2013.01); *C07F 7/1804* (2013.01)

(58) Field of Classification Search
CPC .................................................. C07D 407/14
See application file for complete search history.

(56) References Cited

FOREIGN PATENT DOCUMENTS

| | | |
|---|---|---|
| WO | 2005/118565 A1 | 12/2005 |
| WO | 2009/046308 A1 | 4/2009 |

OTHER PUBLICATIONS

Dong, C-G, et al. "New Syntheses of E7389 C14-C35 and Halichondrin C14-C38 Building Blocks: Reductive Cyclization and Oxy-Michael Cyclization Approaches." J. American Chem. Soc. (2009), vol. 131, pp. 15642-15646.*
Dong, C-G, et al. "New Syntheses of E7389 C14-C35 and Halichondrin C14-C38 Building Blocks: Reductive Cyclization and Oxy-Michael Cyclization Approaches." J. American Chem. Soc. (2009), vol. 131, pp. 15642-15646. (Year: 2009).*
Compound Summary for CID 68014084, Nov. 30, 2012, pp. 1-11, Retrieved from the Internet: URL:http://pubchem.ncbi.nlm.nih.gov/compound/68014084#x304 [retrieved on Jan. 14, 2016].
Austad, et al., Commercial Manufacture of Halaven: Chemiselective Transformations En Route to Structurally Complex Macycyclic Ketones, Synlett (2013) 24, pp. 0333-0337.
Greene, et al., Chapter 2: Protection for the Hydroxyl Group, Including 1,2- and 1,3-Dials, Protective Groups in Organic Synthesis, Jan. 1, 1999, pp. 17-245.
Liu, et al., Dramatic Improvement in Catalyst Loadings and Molar Ratios of Coupling Partners for Ni/Cr-Mediated Coupling Reactions: Heterobimetallic Catalysts, Journal of Am. Chem. Soc. (2009) vol. 131, No. 46, pp. 16678-16680.
Liu, et al., Synthesis of Alcohols from m-Fluorophenylsulfones and Dialkylboranes: Application to the C14-C35 Building Block of E7389, Organic Letters (2012) vol. 14, No. 9, pp. 2262-2265.
Wan, et al., Asymmetric Ni(II)/Cr(II)-Mediated Coupling Reaction: Stoichiometric Process, Organic Letters (2002) vol. 4, No. 25, pp. 4431-4434.

* cited by examiner

*Primary Examiner* — Andrew D Kosar
*Assistant Examiner* — John S Kenyon
(74) *Attorney, Agent, or Firm* — Kramer Amado, P.C.

(57) ABSTRACT

The present invention discloses a novel process for the preparation of macrocyclic ketone analogs of halichondrin B or pharmaceutically acceptable salts thereof and to novel intermediates which are produced during the course of carrying out the novel process.

19 Claims, No Drawings

PROCESS FOR THE PREPARATION OF MACROCYCLIC KETONE ANALOGS OF HALICHONDRIN B OR PHARMACEUTICALLY ACCEPTABLE SALTS AND INTERMEDIATES THEREOF

FIELD OF THE INVENTION

The present invention relates to a novel process for the preparation of macrocyclic ketone analogs of halichondrin B or pharmaceutically acceptable salts thereof and to novel intermediates which are produced during the course of carrying out the novel process.

BACKGROUND OF THE INVENTION

Halichondrin B is a large naturally occurring polyether macrolide originally isolated from the marine sponge *Halichondria okadai* with potent antiproliferative activities.

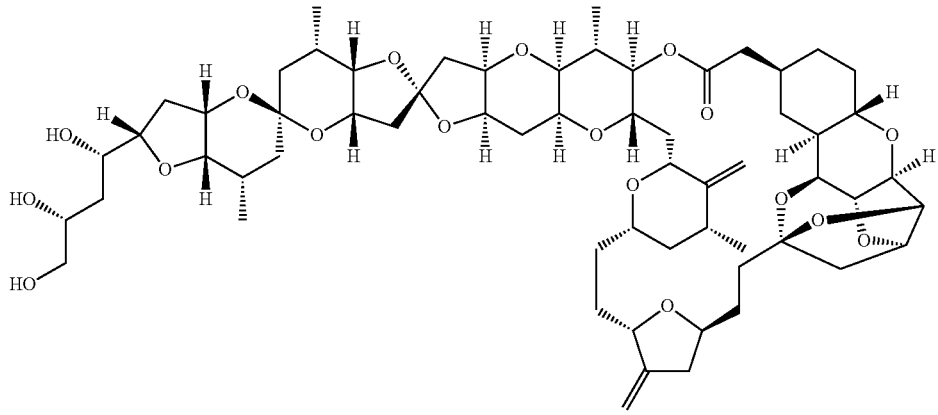

Halichondrin B

A total synthesis of Halichondrin B was published in 1992 (Aicher, T. D. et al. , J. Am. Chem. Soc. 114:3162-3164).

Eribulin, a synthetic macrocyclic ketone analogs of halichondrin B with potent antiproliferative activities is an anticancer drug marketed by Eisai Co, under the trade name Halaven and it is also known as E7389, B1939 and ER-086526.

It was first reported in U.S. Pat. No. 6,214,865. Accordingly, new methods for the synthesis of halichondrin B analogs and particularly, eribulin useful as anti-cancer agents are desirable.

Objects of the Invention

The object of the present invention is to provide a novel process for preparation of halichondrin B analogs or pharmaceutically acceptable salts thereof.

Yet another object of the present invention is to provide a novel process via new intermediates for the synthesis of halichondrin B analogs or pharmaceutically acceptable salts thereof.

Yet another object of the present invention is to provide a process which is simple, economical and suitable for industrial scale-up.

Statements of Invention

According to a first aspect of the present invention, there is provided compounds useful in the synthesis of halichondrin B analogs and particularly, eribulin or pharmaceutically acceptable salts thereof.

In one aspect, the invention provides compound of Formula (I):

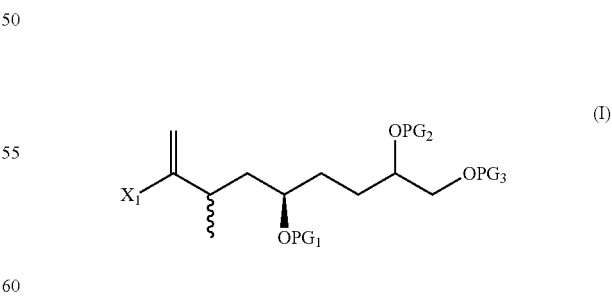

wherein $PG_1$, $PG_2$, $PG_3$ and $X_1$ are as described herein.

In yet another aspect, the invention provides compound of Formula (III):

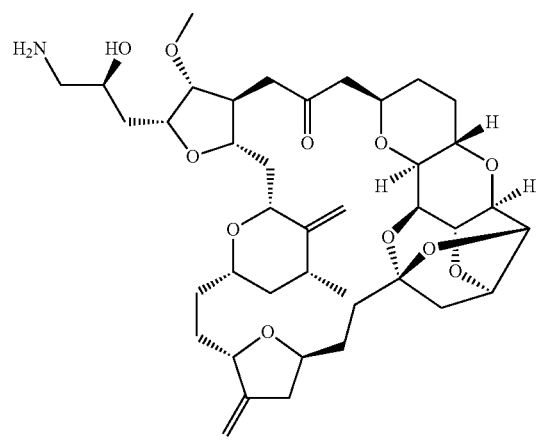 [SMILES: C=C1C[C@@H]2CC[C@@]34C[C@H]5O[C@@H]6[C@@H](O3)[C@H]3O[C@H](CC[C@@H]3O[C@H]6[C@H]5O4)CC(=O)C[C@@H]3[C@@H](OC)[C@@H](C[C@H](O)CN)O[C@H]3C[C@H]3O[C@@H](CC[C@@H]1O2)C[C@@H](C)C3=C]

(III)

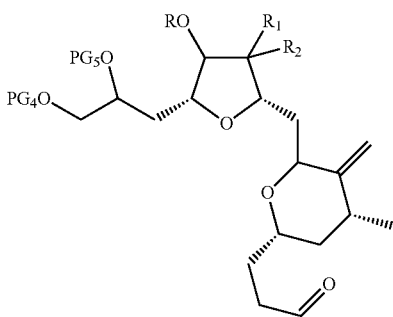

wherein PG$_4$, PG$_5$, R, R$_1$ and R$_2$ are as described herein.

In yet another aspect, the invention provides compound of Formula (V):

(V)

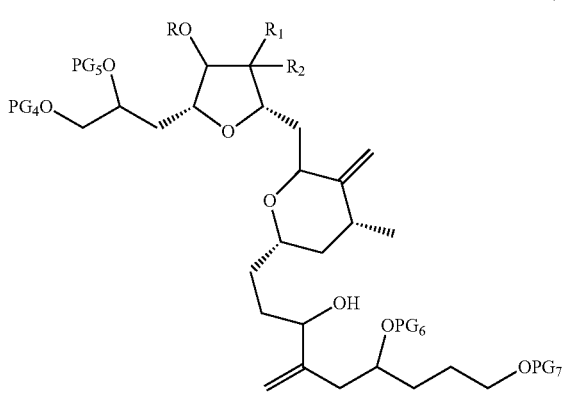

wherein PG$_4$, PG$_5$, PG$_6$, PG$_7$, R, R$_1$ and R$_2$ are as described herein.

In another aspect, the invention provides compound of Formula (VII);

(VII)

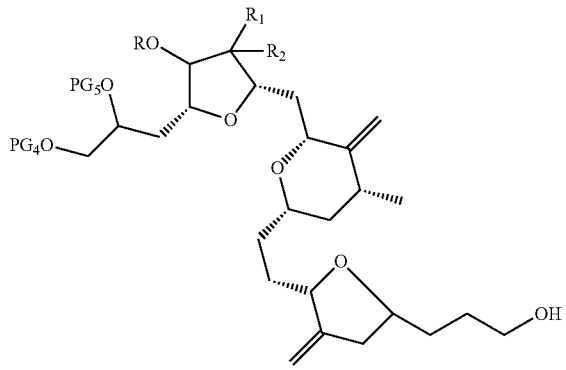

In yet another aspect, the invention provides a process to prepare halichondrin analogs and particularly, eribulin or pharmaceutically acceptable salts thereof, from the compound of Formula I, III, V and VII.

The halichondrin analogs and particularly, eribulin or pharmaceutically acceptable salts thereof, so prepared may be formulated with one or more pharmaceutically acceptable excipients to provide a pharmaceutical composition. Such excipients and compositions are well known to those skilled in the art.

The details of one or more embodiments of the invention are set forth in the description below. Other features, objects, and advantages of the invention will be apparent from the description and from the claims.

DETAILED DESCRIPTION OF THE INVENTION

The present invention provides a process for the preparation of halichondrin B analogs and particularly, eribulin or pharmaceutically acceptable salts thereof, which process is economical, fast and which results in a high purity halichondrin B analogs.

At various places in the present specification, substituents of compounds of the invention are disclosed in groups or in ranges. It is specifically intended that the invention include each and every individual sub combination of the members of such groups and ranges.

For example, the term "C1-6 alkyl" is specifically intended to individually disclose methyl, ethyl, C3 alkyl, C4 alkyl, C5 alkyl, and C6 alkyl.

The term "leaving group" include halide such as chloro, bromo, fluoro, iodo and a sulfonate such as mesylate, besylate, easylate, tosylate, triflate, nonaflate or fluorosulfonate.

The term "hydroxyl protecting groups" include, but are not limited to the protecting groups for hydroxy delineated in Wuts and Greene, Protective Groups in Organic Synthesis, 4th ed., John Wiley & Sons: New Jersey, (2007), which is incorporated herein by reference in its entirety.

In some embodiments, PG is benzyloxycarbonyl (Cbz), 2,2,2-trichloroethoxycarbonyl (Troc), 2-(trimethylsilyl) ethoxycarbonyl (Teoc), 2-(4-20 trifluoro methyl phenyl sulfonyl) ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxy carbonyl (Hoc), 1,1-dimethyl-2,2,2-trichloro ethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP). In some embodiments, PG is tri(C1-4 alkyl)silyl (e.g., tri(isopropyl)silyl). In some embodiments, PG is 1,1-diethoxymethyl In some embodiments, PG is 2-(trimethylsilyl)ethoxymethyl (SEM). In some embodiments, PG is N-pivaloyloxymethyl (POM). In some embodiments, PG forms an ester, such as acetyl, benzoyl or pivaloyl. In some embodiments, PG forms an ether such as β-methoxyethoxymethyl ether (MEM), trityl (Tr), dimethoxy trityl (DMT), methoxymethyl ether (MOM), P-toluenesulphonyl (Ts), tert-butylsilyl (TBS). In some embodiments, PG forms silyl protection such as tert-butyldimethylsilyl (TBDMS), tri-isoprolylsilyloxy methyl (TOM), tri-isopropylsilyl (TIPS).

In one aspect, the present invention provides processes for preparing intermediate compounds useful for producing halichondrin B analogs and particularly, eribulin or pharmaceutically acceptable salts thereof.

In another aspect, the present invention provides intermediate compounds of any of the intermediates described herein.

As described above, the present invention provides intermediate compound of Formula (I)

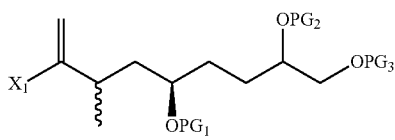

(I)

wherein each of PG$_1$, PG$_2$ and PG$_3$ are independently hydrogen or a hydroxyl protecting group and X$_1$ is leaving group.

In certain embodiment's one, two, or three of PG$_1$, PG$_2$ and PG$_3$, taken with the oxygen atom(s) to which they are bound, are silyl ethers or arylalkyl ether. For example, in other embodiments, one, two, or three of PG$_1$, PG$_2$ and PG$_3$ are t-butyldimethylsilyl (TBS), benzyl (Bz) or tosyl (Ts), or all of PG$_1$, PG$_2$ and PG$_3$ are t-butyldimethylsilyl (TBS) or tosyl (Ts).

In some embodiments, X$_1$ is a halogen, such as iodide. In other embodiments, X$_1$ is (C1-C6)alkylsulfonate, (C6-C 10 aryl or C1-C6 heteroaryl)sulfonate, (C6-C15)aryl(C1-C6) alkyl sulfonate, or (C1-C6)heteroaryl(C1-C6)alkylsulfonate. Specific leaving groups include mesylate, toluenesulfonate, isopropylsulfonate, phenylsulfonate, or benzylsulfonate.

In an embodiment, compound of Formula (I), is prepared by a process which comprises steps of (i) reacting compound of Formula (Ia)

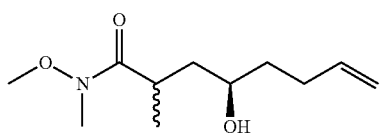

(Ia)

with a protecting agent in the presence of a base to obtain compound of Formula (Ib).

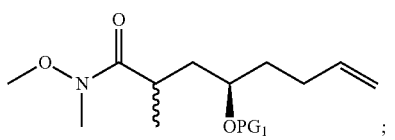

(Ib)

(ii) reacting with a suitable hydroxylating agent, to form vicinal diol of Formula (Ic)

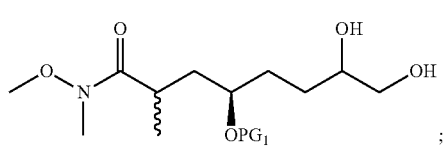

(Ic)

(iii) protecting using suitable protecting agent to form compound of Formula (Id):

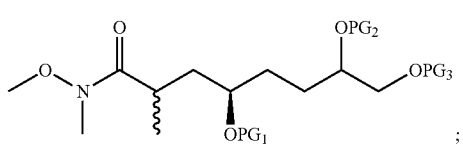

(Id)

(iv) reducing with suitable reducing agent to form compound of Formula (Ie):

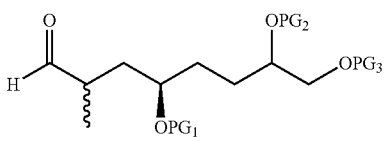

(Ie)

(V) reacting with suitable halogenating agent to form compound of Formula (If):

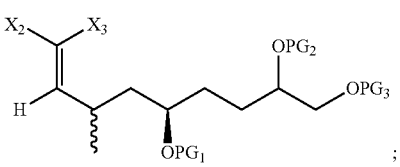

(If)

and (vi) alkynetion and haloboration to form compound of Formula (I);

wherein PG$_1$, PG$_2$ and PG$_3$ are as defined above;

and,

X$_2$ and X$_3$ are leaving group, preferably halide, more preferably bromo.

In some embodiments, the process further comprises preparing the compound of Formula (Ia); by reacting compound of Formula (IIa)

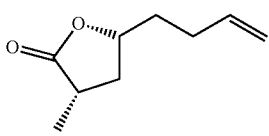

(IIa)

with dimethyl hydroxyl amine.

Accordingly, an embodiment of the process for the preparation of compound of Formula (I) is as shown in Scheme A.

Scheme A

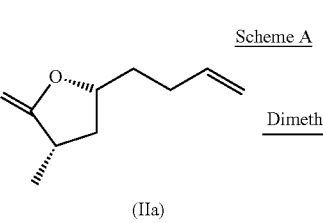

Dimethylhydroxyl amine →

(IIa)

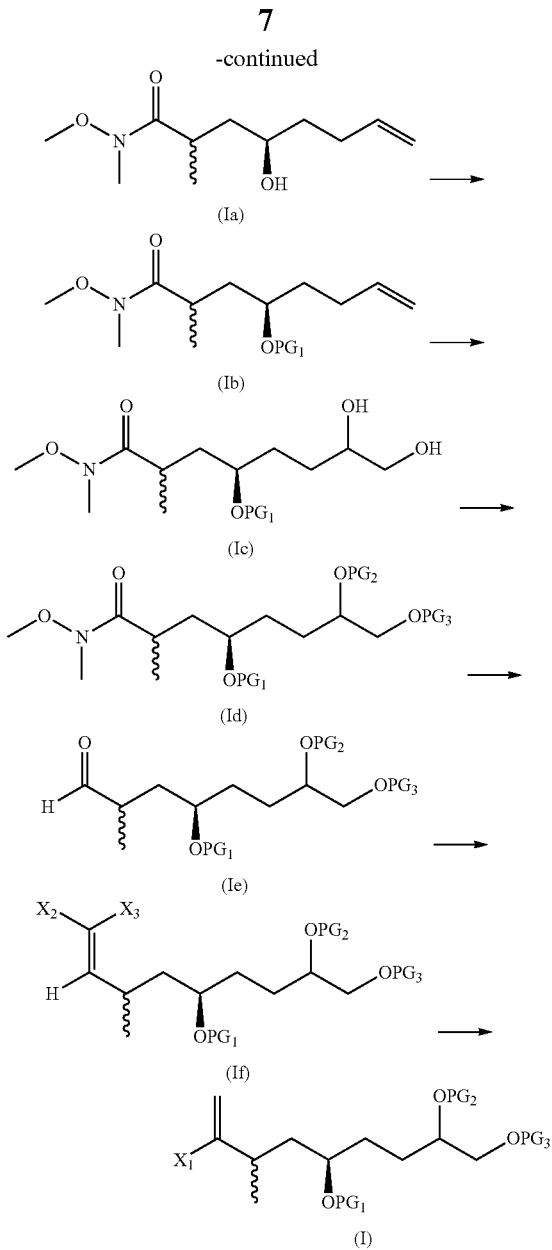

The compounds of Formula Ia, Ib, Ic, Id, Ie, If and I are hitherto unreported intermediates useful in the process for the preparation of halichondrin B analogs as described herein.

In an embodiment lactone of Formula (IIa) is treated with N,O-dimethylhydroxylamine hydrochloride [MeO(Me)NH.HCl] in presence of $AlMe_3$ or $AlMe_2Cl$ to afford the corresponding Weinreb amide of Formula (Ia). Reaction may be performed in a non-polar solvents, such as halogenated solvents like dichloromethane (DCM) and dichloroethane (EDC). Preferably, the reaction is carried out at a temperature in the range of from about −10° C. to about 40° C. for about 1 hour to about 24 hours. More preferably the reaction step is carried out at a temperature in the range from about 0 to about 30° C., for about 3 hours to about 6 hours.

The hydroxyl group on Weinreb amide of Formula (Ia) is further protected using suitable protecting group to obtain compound of Formula (Ib).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents. The protective groups are independently selected from esters, carbonates, carbamates, sulfonates, and ethers.

Preferably, the protection reaction is performed under anhydrous conditions in the presence of a polar protic solvent such as THF using mesyl chloride or tosyl chloride.

Hydroxylation of compound of Formula (Ib) is carried out using dilute potassium permanganate ($KMnO4$) or osmium catalyst. A preferred osmium catalyst is osmium tetroxide ($OsO4$). Optionally, a stoichiometric amount of an oxidant [e.g. $K_3Fe(CN)_6$ or N-methylmorpholine oxide (NMO)] and a buffered solution may be added to ensure a stable pH, since the reaction proceeds more rapidly under slightly basic conditions. Alternatively, hydroxylation may be carried out by the Woodward Reaction to give corresponding diol of Formula (Ic) which is further protected using suitable protecting group to give compound of Formula (Id).

Preferably, the hydroxylation is performed in the presence of aqueous solvents at a temperature in the range of from about −10° C. to about 30° C. for about 1 hour to about 24 hours.

Weinreb amide of Formula (Id) is further reduced with DIBAL-H or an excess of lithium aluminum hydride to aldehyde of Formula (Ie).

The reduction step is performed in the presence of polar aprotic solvent such as THF under inert atmosphere at a temperature in the range of from about −10° C. to about 10° C. for about 30 minutes to about 5 hours.

Suitable halogenating agent include but not limited to $CBr_4$ in combination with triphenyl phosphine (Corey-Fuchs reaction) to transform an aldehyde of Formula (Ie) into 1,1-dibromoolefins of Formula (If), which is further converted to an alkyne.

The halogenation step is performed in the presence of halogenated solvents such as DCM at a temperature in the range of from about −10° C. to about 30° C. for about 30 minutes to about 5 hours. In one aspect, it is carried out at a temperature in the range of from about 10° C. to about 20° C. for about 1 to about 2 hours.

Deprotonation of 1,1-dibromoolefins of Formula (If) with butyllithium gives rise to internal alkyne, which further undergoes haloboration with B-Bromo- or B-iodo-9-borabicyclo[3.3.1]-nonane (B-X-9-BBN) and other haloboranes to give corresponding 1-halo-1-alkenes of Formula (I).

The deprotonation reaction step is performed under anhydrous conditions in the presence of polar aprotic solvent such as THF at a temperature in the range of from about −78° C. to about −70° C. for about 1 to 2 hours. The intermediate alkyne is not isolated and undergoes haloboration reaction at room temperature for about 1 to 5 hours to yield compound (I).

In one preferred embodiment, when X1 is iodo, X2 and X3 are bromo, PG1 is methane sulfonyl (mesyl/Ms), PG2 and PG3 are t-butyldimethyl silyl (TBS), the compound (I) obtained by the process of the invention includes compound of formula (I)-A:

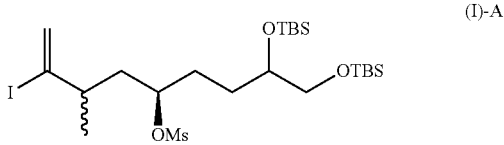 [SMILES: C=C(I)C(C)C[C@@H](CCC(CO[Si](C)(C)C(C)(C)C)O[Si](C)(C)C(C)(C)C)OS(C)(=O)=O]

Accordingly, a process for preparing a compound of formula (I)-A according to the present invention is exemplified in Scheme A1.

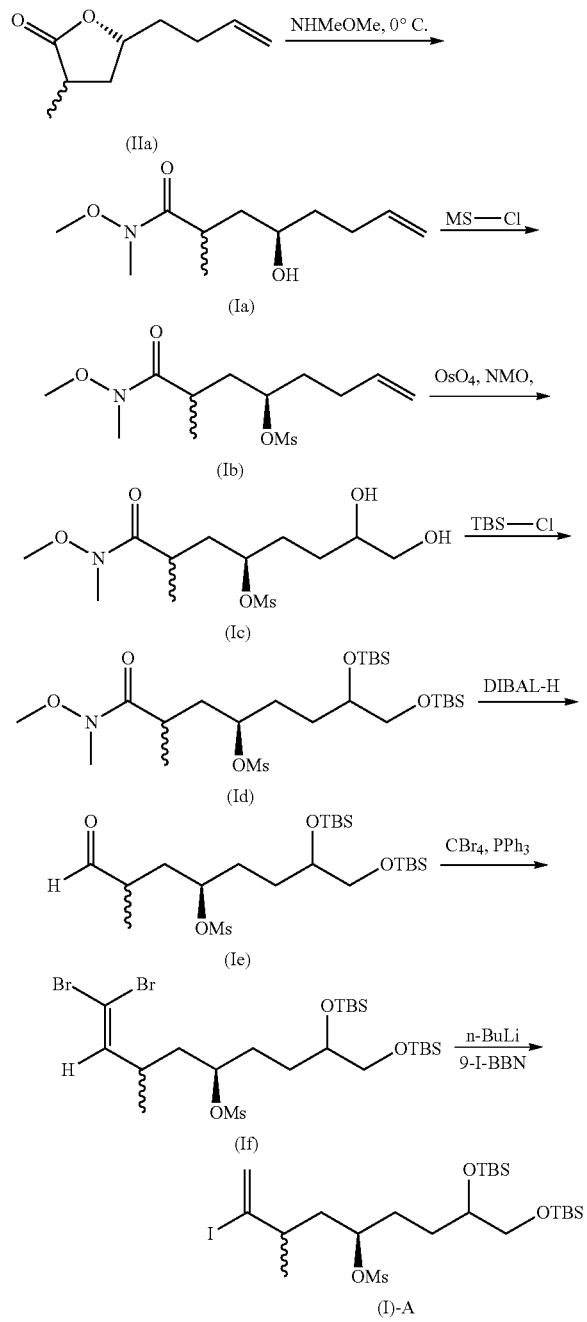

The compounds of Formula Ia, Ib, Ic, Id, Ie, If and I-A are hitherto unreported intermediates useful in the process for the preparation of halichondrin B analogs as described herein.

In yet another aspect, the invention provides compound of Formula (III).

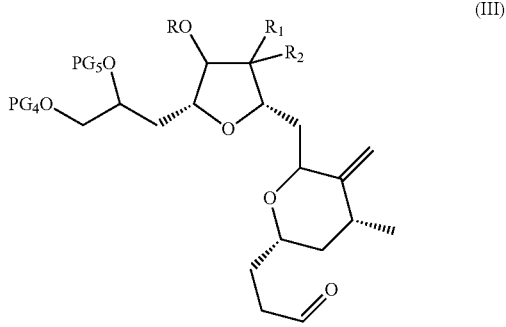

wherein each of $PG_4$ and $PG_5$ are independently H or C1-6 alkyl; or $PG_4$ and $PG_5$, together with the oxygen atoms to which they are attached, form a diol protecting 5- to 6-membered heterocyclic ring, which is optionally substituted with C1-4 alkyl groups. Diol protecting groups are well known in the art and include cyclohexylidene and benzylidene diol protecting group.

In certain embodiments, one or both of $PG_4$ and $PG_5$ of Formula (III), taken with the oxygen atom(s) to which they are bound, are silyl ethers or arylalkyl ethers. For example, one or both of $PG_4$ and $PG_5$ are TBS or benzyl, or both $PG_4$ and $PG_5$ are TBS; $R_1$ and $R_2$ each independently is H, —$CH_2OR_3$ or —$CH_2SO_2Ar$, or $R_1$ and $R_2$ together form =$CH_2SO_2Ar$, wherein $R_3$ is H or a hydroxyl protecting group; and Ar is an aryl group;

In one embodiment R is H, C1-6 alkyl or C1-6 haloalkyl. In a further embodiment R is C1-6 alkyl. In a preferred embodiment R is methyl.

In an embodiment, compound of Formula (III), is prepared by a process which comprises steps of;

(i) intramolecular coupling (Nozaki-Hiyama-Kishi [NHK] coupling) of compound of Formula (I) with compound of Formula (II)

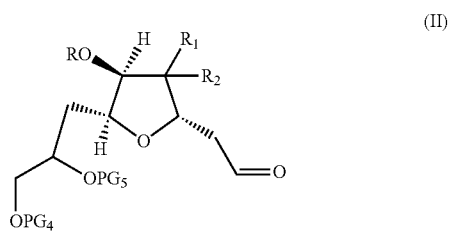

to form compound of Formula (IIIa):

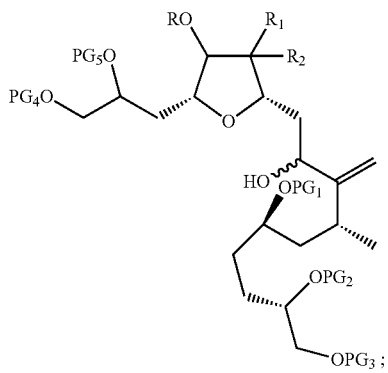

(ii) intramolecular cyclization (oxy-Michael ring closure) to form compound of Formula (IIIb):

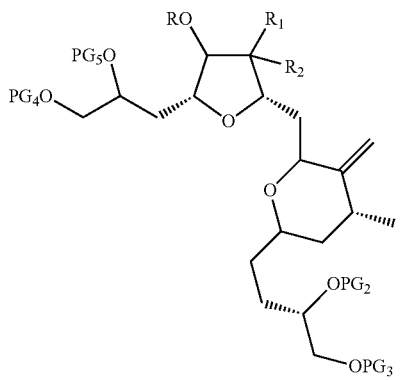

(iii) removal of protecting group to form compound of Formula (IIIc):

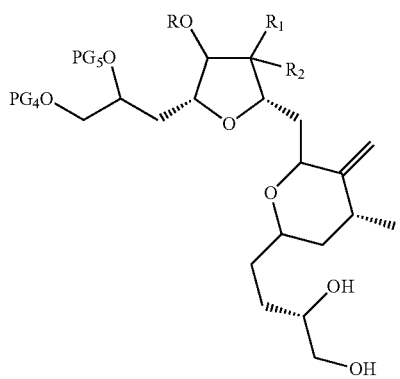

and (iv) reducing with suitable reducing agent to form compound of Formula (III)

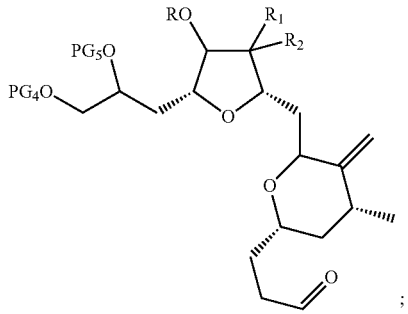

wherein $PG_1$, $PG_2$, $PG_3$, $PG_4$, $PG_5$, $X_1$, R, $R_1$ and $R_2$ are as defined above Accordingly, an embodiment of the process for the preparation of compound of Formula (III) is as shown in Scheme B.

Scheme B

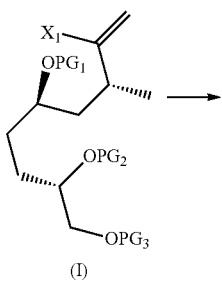

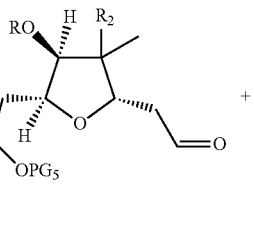

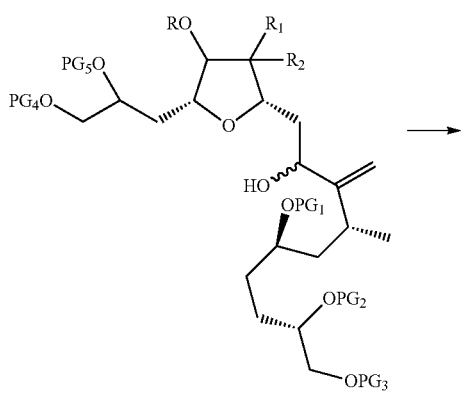

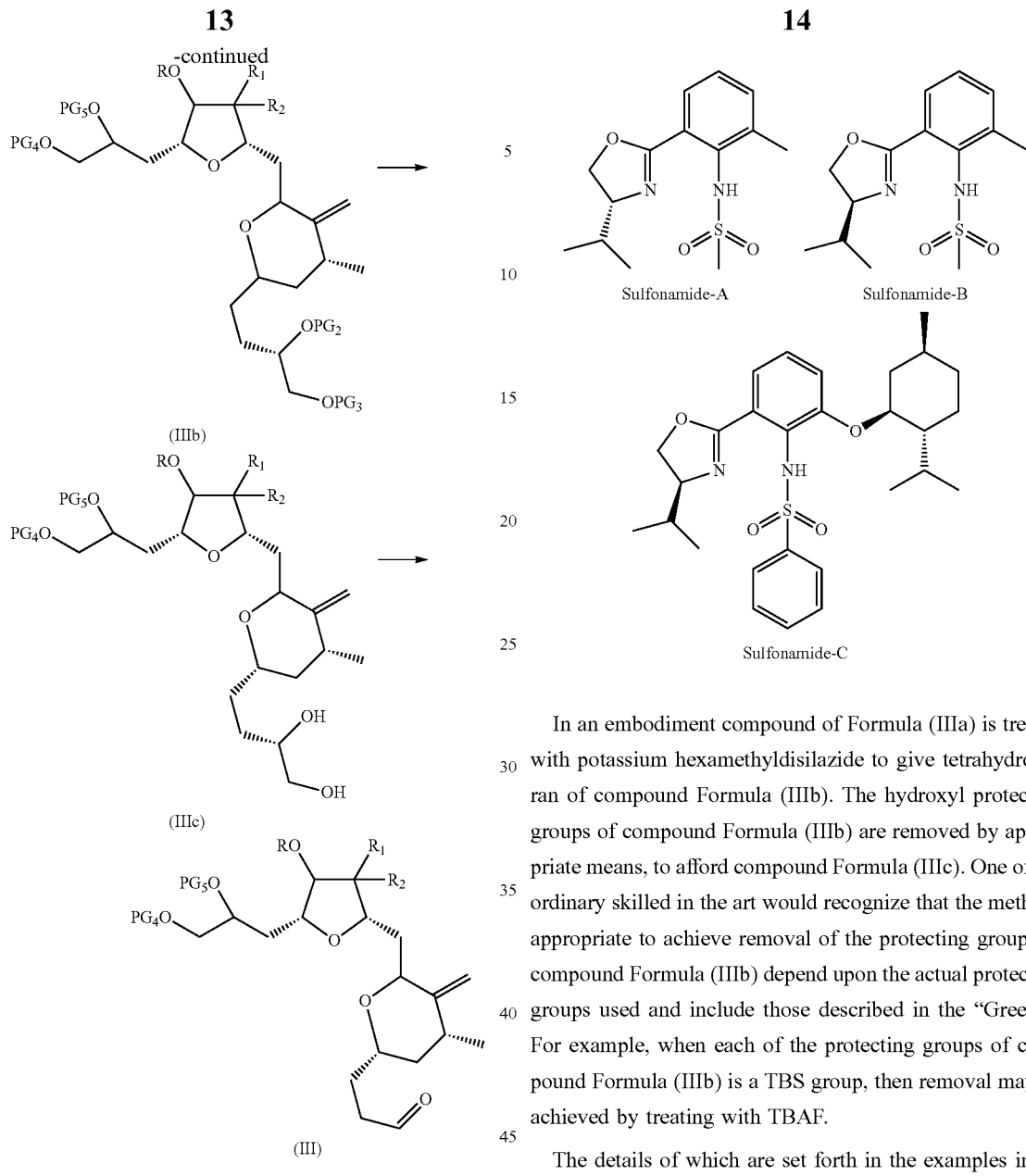

In an embodiment compound of Formula (IIIa) is treated with potassium hexamethyldisilazide to give tetrahydropyran of compound Formula (IIIb). The hydroxyl protecting groups of compound Formula (IIIb) are removed by appropriate means, to afford compound Formula (IIIc). One of the ordinary skilled in the art would recognize that the methods appropriate to achieve removal of the protecting groups of compound Formula (IIIb) depend upon the actual protecting groups used and include those described in the "Greene". For example, when each of the protecting groups of compound Formula (IIIb) is a TBS group, then removal may be achieved by treating with TBAF.

The details of which are set forth in the examples infra.

The vicinal diol compound of Formula (IIIc) is then treated with sodium periodate to form aldehyde compound Formula (III). Addition of 2,6-lutidine can suppress the side reactions and improve the yield of the reaction. Alternatively, vicinal diol compound of Formula (IIIc) may be treated with oxidants like periodic acid (HIO4) and lead tetra-acetate [Pb(OAc)$_4$] to form carbonyl compound of Formula (III).

In one preferred embodiment, when $X_1$ is iodo, R is methyl, $R_1$ and $R_2$ together form $CH_2SO_2Ph$, $PG_1$ is methane sulfonyl (mesyl/Ms), $PG_2$ and $PG_3$ are t-butyldimethyl silyl (TBS), $PG_4$ and $PG_5$ together with the oxygen atoms to which they are attached, form a diol protecting 5 membered heterocyclic ring, which is optionally substituted with methyl groups; the compound (III) obtained by the process of the invention includes compound of formula (III)-A:

The compounds of Formula IIIa, IIIb, IIIc and III are hitherto unreported intermediates useful in the process for the preparation of halichondrin B analogs as described herein.

In an embodiment, an intramolecular coupling reaction of halide of Formula (I) and aldehyde of Formula (II), is a chromium-induced redox reaction. The coupling reaction is, Cr—Ni bimetallic catalyst-promotes redox addition of vinyl halides to aldehydes. A key advantage is the high chemoselectivity toward aldehydes. Alternatively, catalytic amount of chromium(II) which is regenerated by reduction with manganese or via electrochemical reduction, or palladium acetate may be added as co-catalyst to enhance the rate of the reaction. In a preferred embodiment the catalyst used for the coupling reaction is NiCl$_2$/CrCl$_2$.

The coupling is preferably carried in the presence of a ligand and polar aprotic solvent such as THF, DMSO, and acetonitrile at room temperature for about 5 to 10 hours. The ligand used is preferably selected from sulfonamide ligands such as sulfonamide-A, sulfonamide-B and sulfonamide-C.

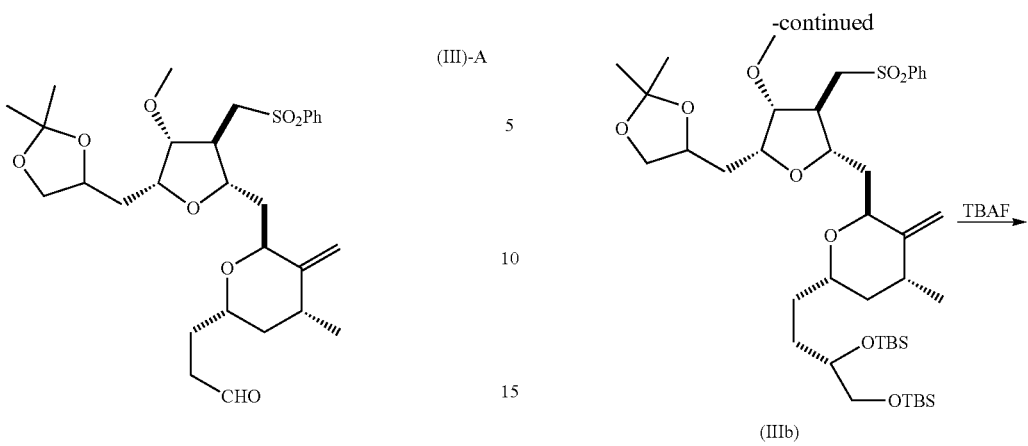

Accordingly, a process for preparing a compound of formula (III)-A according to the present invention is exemplified in Scheme B1

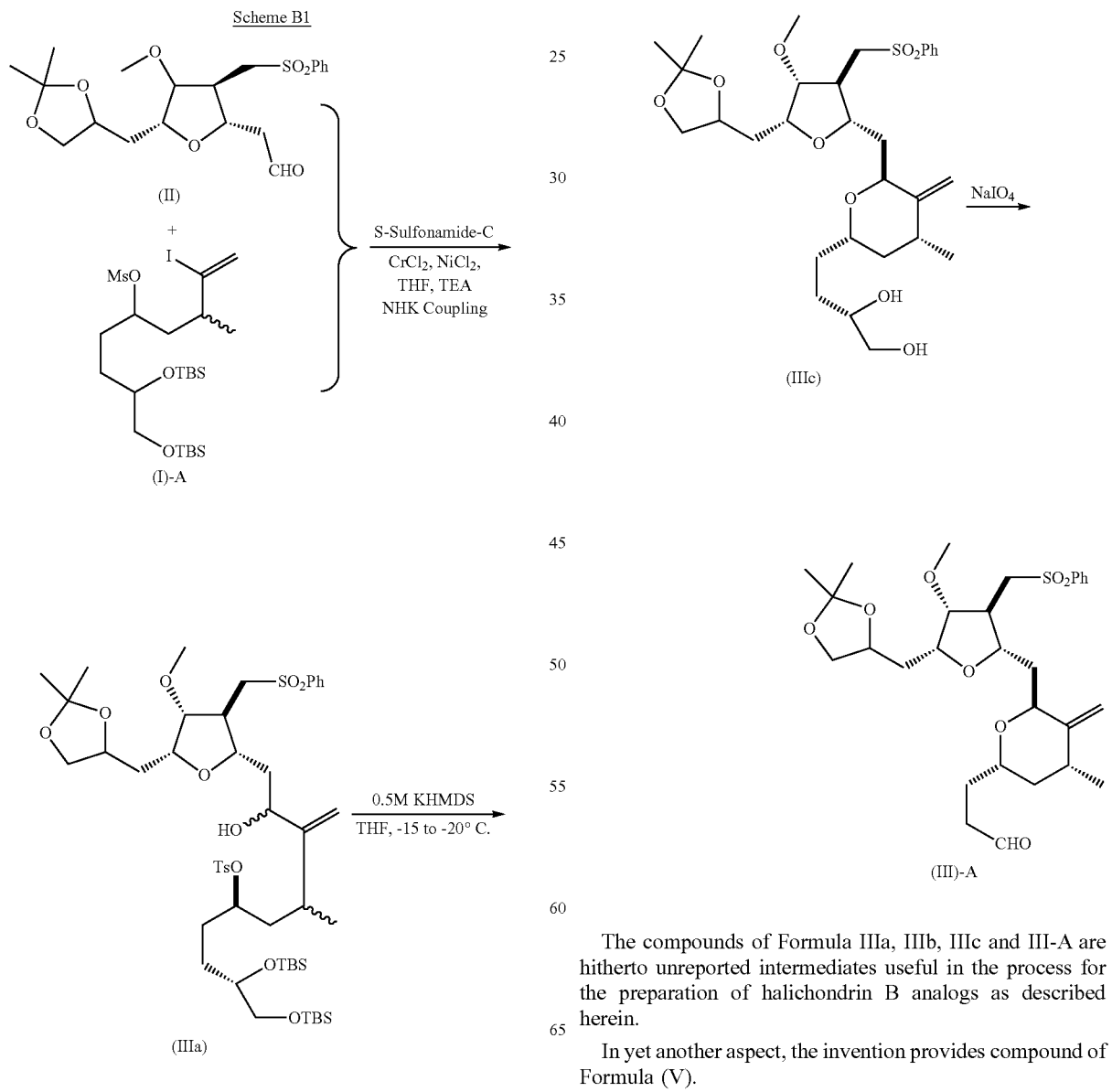

The compounds of Formula IIIa, IIIb, IIIc and III-A are hitherto unreported intermediates useful in the process for the preparation of halichondrin B analogs as described herein.

In yet another aspect, the invention provides compound of Formula (V).

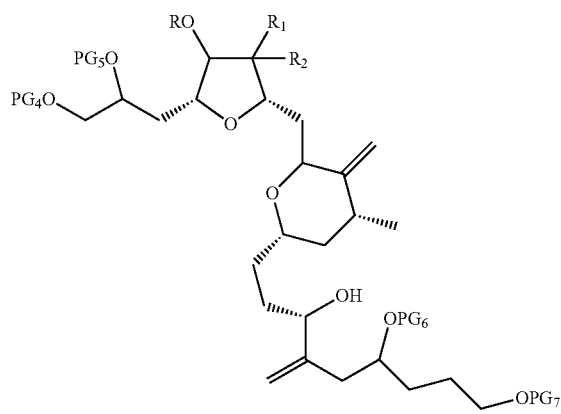
(V)

In an embodiment, compound of Formula (V), is prepared by a process which comprises; intramolecular coupling (NHK coupling) of compound of Formula (III) with compound of Formula (IV)

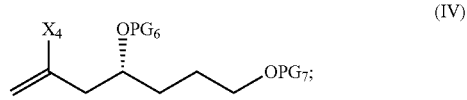
(IV)

wherein $PG_4$, $PG_5$, R, $R_1$ and $R_2$ are as defined above and each of $PG_6$ and $PG_7$ are independently hydrogen or a hydroxyl protecting group and $X_4$ is a leaving group.

Accordingly, an embodiment of the process for the preparation of compound of Formula (V) is as shown in Scheme C.

Scheme C

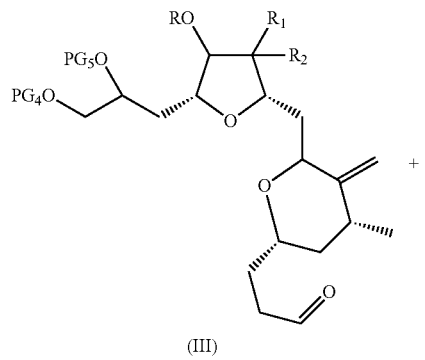
(III)

+

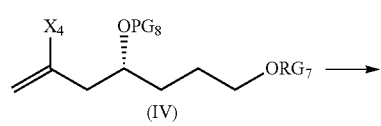
(IV)

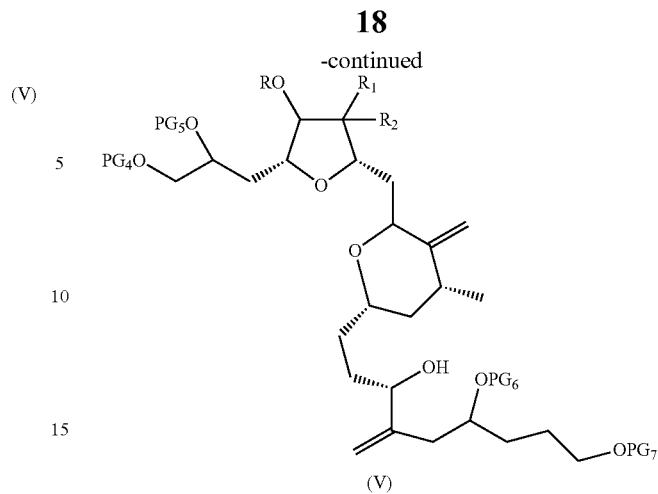
(V)

The compound of Formula V is hitherto unreported intermediate useful in the process for the preparation of halichondrin B analogs as described herein.

In an embodiment, compound of Formula (III) is subjected to an intramolecular coupling reaction with compound of Formula (IV) in the presence of a base and a suitable solvent, under conditions similar to those involved in the coupling of compound of Formula (I) with (II).

In one preferred embodiment, when $X_4$ is bromo, R is methyl, $R_1$ and $R_2$ together form $CH_2SO_2Ph$, $PG_4$ and $PG_5$ together with the oxygen atoms to which they are attached, form a diol protecting 5 membered heterocyclic ring optionally substituted with methyl groups, $PG_6$ is mesyl (Ms) and $PG_7$ is t-butyl diphenyl silyl (TBDPS); the compound (V) obtained by the process of the invention includes compound of formula (V)-A:

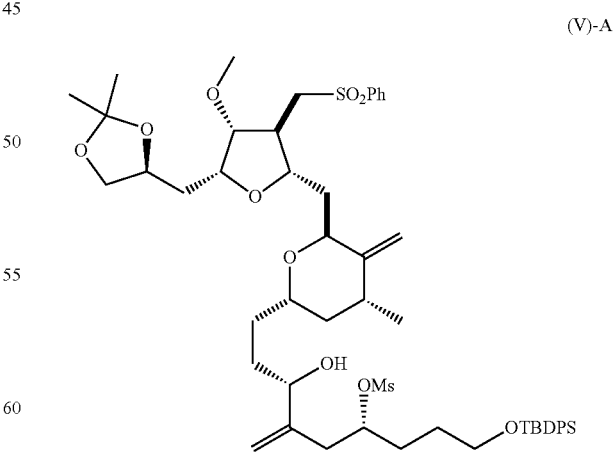
(V)-A

Accordingly, a process for preparing a compound of formula (V)-A according to the present invention is exemplified in Scheme C1

Scheme C1

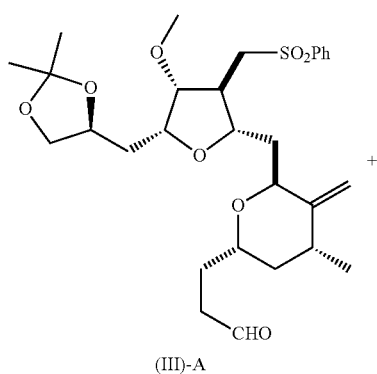

(III)-A

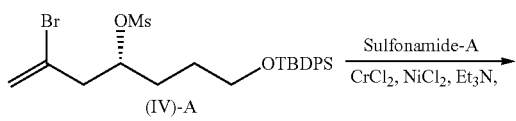

(IV)-A

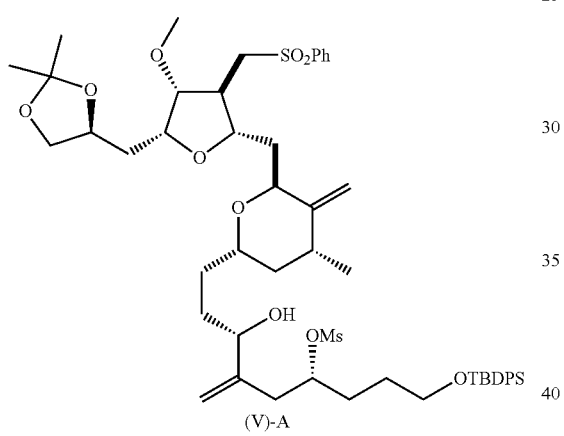

(V)-A

In yet another aspect, the invention provides compound of Formula (VII).

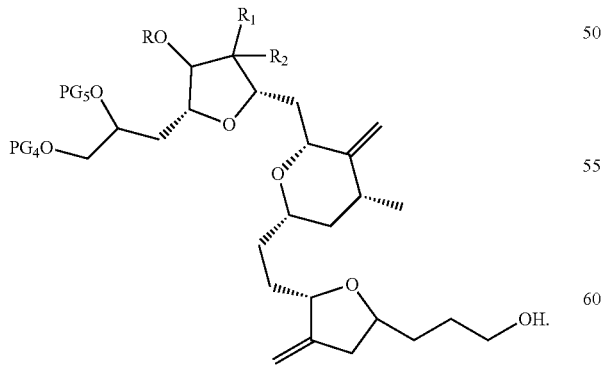

In yet another aspect, the invention provides a process for converting compound of Formula (V) into compound of Formula (VII);

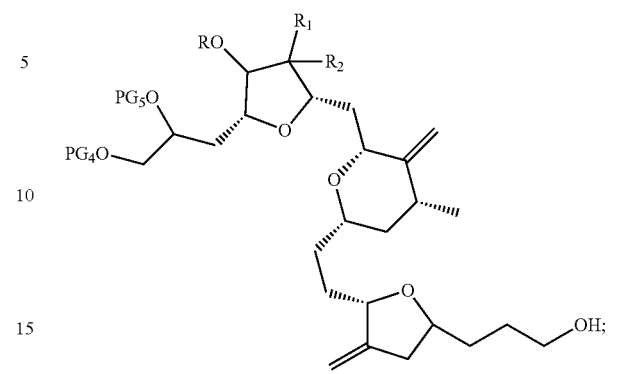

comprising steps of:
(i) intramolecular cyclization (oxy-Michael ring closure) of compound of Formula (V) to form compound of Formula (VI):

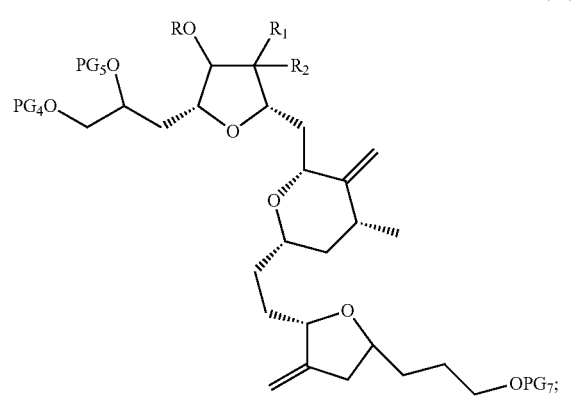

and
(ii) removal of protecting group to form compound of Formula (VII);
wherein $PG_4$, $PG_5$, $PG_6$, $PG_7$, R, $R_1$ and $R_2$ are as defined above.

Accordingly, an embodiment of the process for the preparation of compound of Formula (VII) is as shown in Scheme D.

Scheme D

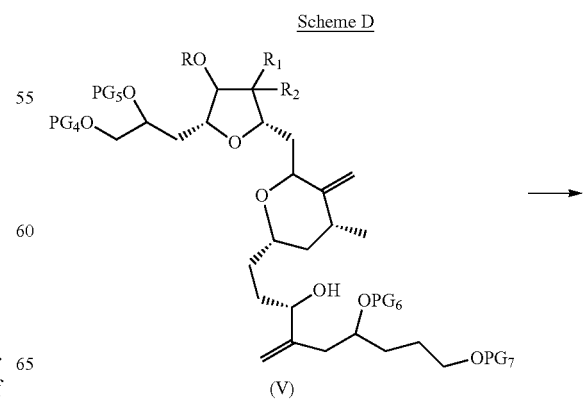

(V)

-continued

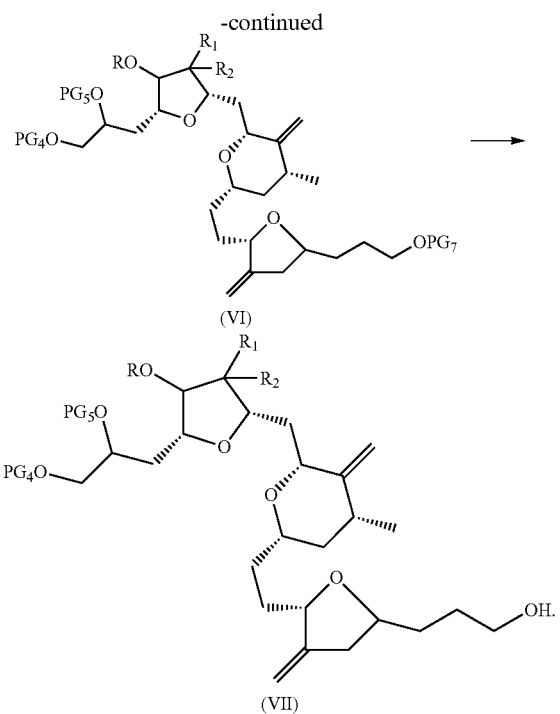

(VI)

(VII)

The compounds of Formula VI and VII are hitherto unreported intermediates useful in the process for the preparation of halichondrin B analogs as described herein.

In an embodiment, compound of Formula (V) is treated with either SiO$_2$ or PPTS in presence of a suitable solvent such as isopropyl alcohol and a base such as pyridine for a period of 2 hours to 4 days at 25-50° C. to obtain cyclic ketone of Formula (VI). The hydroxyl protective group is then chemoselectively deprotected using HCl, TTAF, LiOAc or DBU using suitable polar solvent like THF and IPA to obtain compound of Formula (VII).

In one preferred embodiment, R is methyl, R$_1$ and R$_2$ together form CH$_2$SO$_2$Ph, PG$_4$ and PG$_5$ together with the oxygen atoms to which they are attached, form a diol protecting 5 membered heterocyclic ring optionally substituted with methyl groups; the compound (VII) obtained by the process of the invention includes compound of formula (VII)-A:

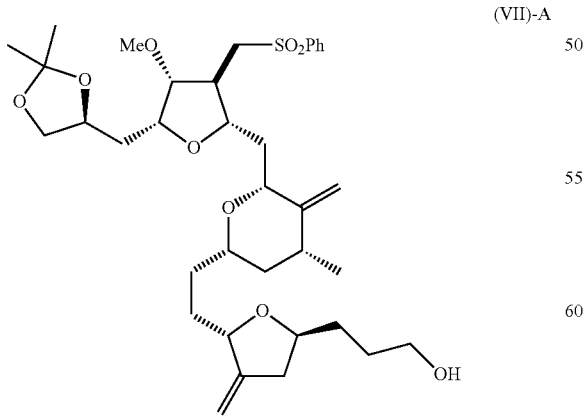

(VII)-A

In a preferred embodiment compound (V)-A is converted to compound (VII)-A as shown in Scheme D1

Scheme D1

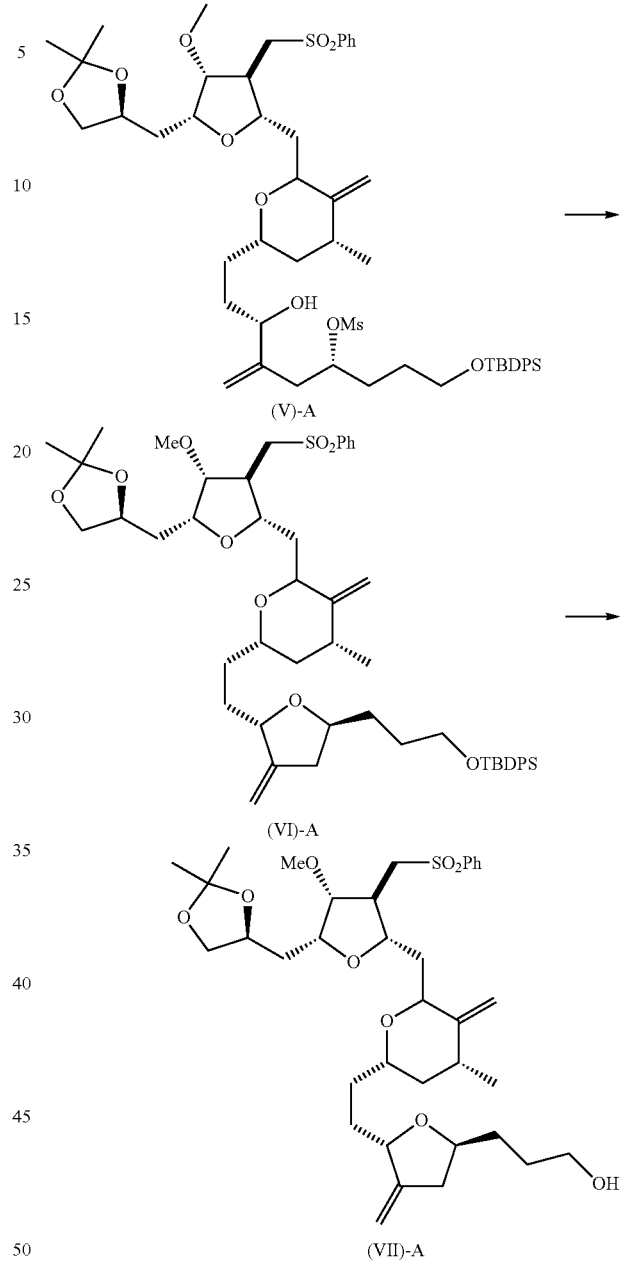

(V)-A (VI)-A (VII)-A wherein R is methyl, R$_1$ and R$_2$ together form CH$_2$SO$_2$Ph, PG$_4$ and PG$_5$ together with the oxygen atoms to which they are attached, form a diol protecting 5 membered heterocyclic ring which is optionally substituted with methyl groups, PG$_6$ is mesyl (Ms) and PG$_7$ is t-butyl diphenyl silyl (TBDPS).

The compounds of Formula (VI)-A and (VII)-A are hitherto unreported intermediates useful in the process for the preparation of halichondrin B analogs as described herein.

In yet another aspect, the invention provides a process for converting compound of Formula (VII) prepared by the process of the present invention into halichondrin analogs and particularly, eribulin or pharmaceutically acceptable salts thereof.

Accordingly, an embodiment of the process for the preparation of eribulin is as shown in Scheme E.

Scheme E
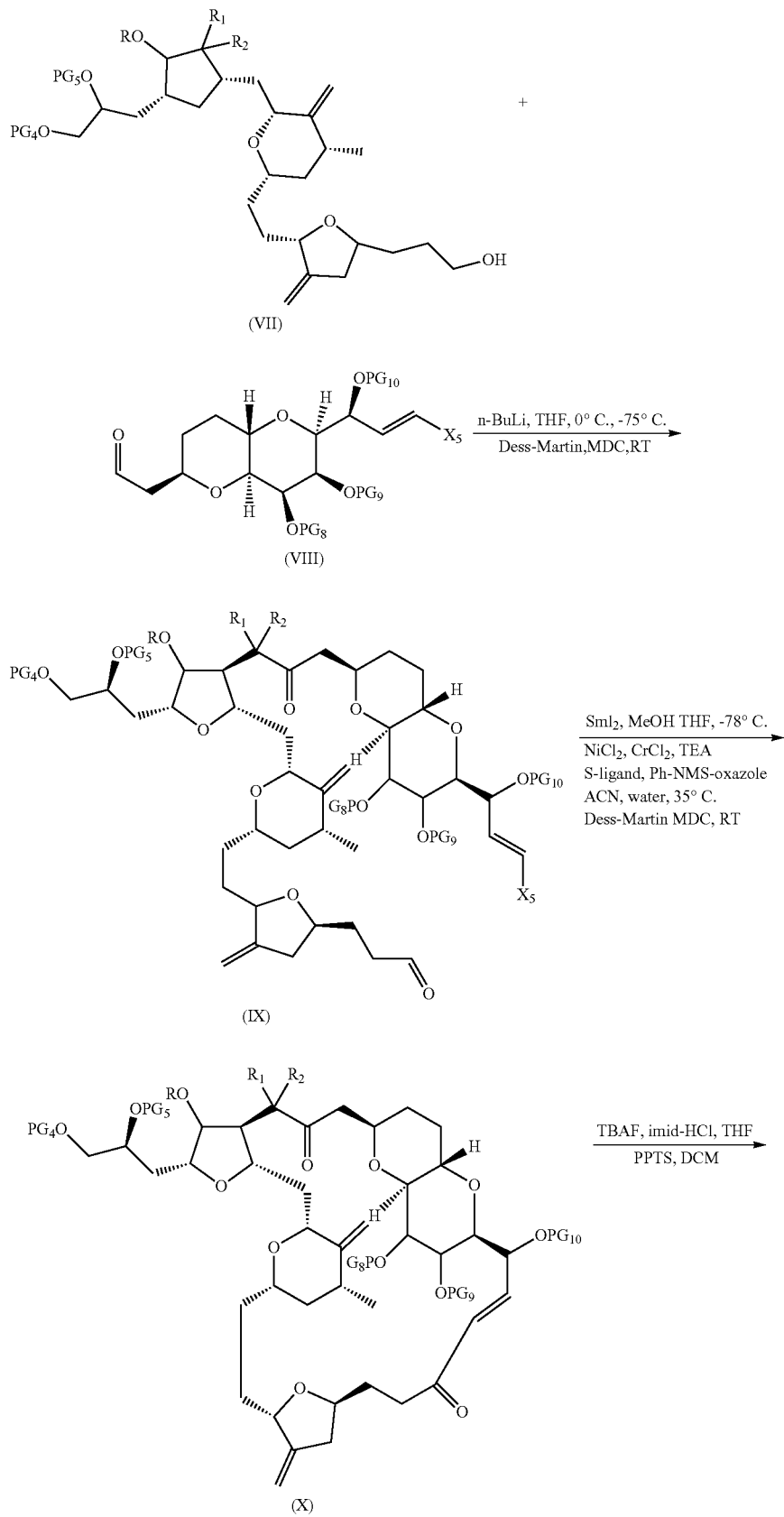

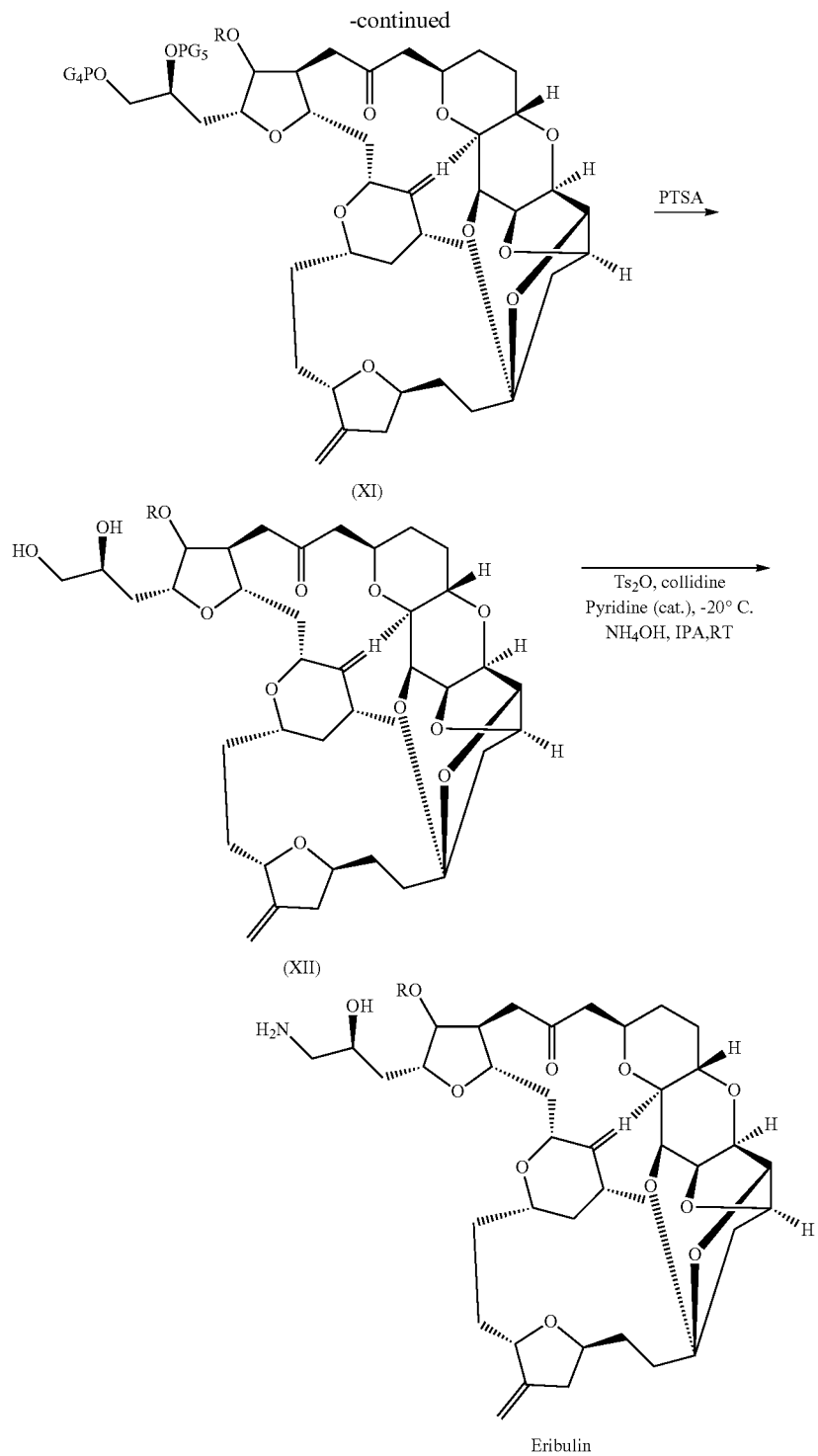

wherein R is methyl; PG$_4$, PG$_5$, R$_1$ and R$_2$, are as defined above, and wherein each of PG$_8$, PG$_9$, and PG$_{10}$ are each independently H or C1-6 alkyl or a hydroxyl protecting group; and X$_5$ is a leaving group.

The compounds of Formula IX, X and XI are hitherto unreported intermediates useful in the process for the preparation of halichondrin B analogs as described herein.

In certain embodiments, one, two, or three of PG$_8$, PG$_9$, and PG$_{10}$ of Formula (VIII), taken with the oxygen atom(s) to which they are bound, are silyl ethers or arylalkyl ethers. For example, one, two, or three of PG$_8$, PG$_9$, and PG$_{10}$ of Formula (VIII) are t-butyldimethylsilyl (TBS) or benzyl, or all of PG$_8$, PG$_9$, and PG$_{10}$ of Formula (VIII) are t-butyldimethylsilyl (TBS). In other embodiments, X$_3$ is a halogen, (C1-C6)alkylsulfonate, (C6-C10 aryl or C1-C6 heteroaryl) sulfonate, (C6-C15)aryl(C1-C6)alkylsulfonate, or (C1-C6) heteroaryl (C1-C6)alkyl sulfonate. Specific examples of X$_3$ include iodide, mesylate, toluenesulfonate, isopropylsulfonate, phenylsulfonate, nitro-phenylsulfonate (nosylate), and bromo-phenylsulfonate (brosylate), and benzylsulfonate.

In certain embodiments, one or both of $PG_8$, $PG_9$, and $PG_{10}$ of Formula (VIII), taken with the oxygen atom(s) to which they are bound, are independently selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chloro phenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloro ethyl, 2-(trimethylsilyl)ethyl, 2-(phenylsulfonyl)ethyl, vinyl, allyl, and p-nitrobenzyl.

Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy) methyl, benzyloxymethyl, beta(trimethylsilyl) ethoxymethyl, and tetrahydro pyranyl ethers. Examples of arylalkyl ethers include benzyl, p-methoxybenzyl (MPM), 3,4-dirnethoxybenzyl, o-nitrobenzyl, pnitrobenzyl, p-halobenzyl, 2,6-dichlorobenzyl, p-cyanobenzyl, 2- and 4-picolyl.

For example, in other embodiments, one, two, or three of $PG_8$, $PG_9$, and $PG_{10}$ are t-butyldimethylsilyl (TBS), benzyl (Bz) or tosyl (Ts), or all of $PG_8$, $PG_9$, and $PG_{10}$ are t-butyldimethylsilyl (TBS) or tosyl (Ts).

In some embodiments $PG_8$ and $PG_9$, together with the oxygen atoms to which they are attached, form a diol protecting 5- to 6-membered heterocyclic ring, which is optionally substituted with C1-4 alkyl groups. In other embodiments, $PG_8$ and $PG_9$ are taken together to form a cyclohexylidene protecting group.

In some embodiments $X_5$ is halogen, such as iodide. In other embodiments, $X_5$ is (C1-C6)alkylsulfonate, (C6-C10 aryl or C1-C6 heteroaryl)sulfonate, (C6-C 15)aryl(C1-C6) alkyl sulfonate, or (C1-C6)heteroaryl(C1-C6)alkylsulfonate. Specific leaving groups include mesylate, toluenesulfonate, isopropylsulfonate, phenylsulfonate, or benzylsulfonate.

In an embodiment, compound of Formula (VII) is coupled with compound of Formula (VIII) in the presence of a base and a suitable solvent, similar to those as noted herein and disclosed in U.S. Pat. No. 6,214,865 B1 (incorporated herein by reference) to form an intermediate alcohol. This is followed by oxidation of the alcohol using reagents to give the compound of Formula (IX). Preferably, compound of Formula (VII) is treated with n-butyllithium then with the aldehyde of Formula (VIII). The resulting diol intermediate is then oxidized with Dess-Martin reagent to form the ketone-aldehyde intermediate of Formula (IX).

The compound of Formula (IX) is subjected to the reduction of the arylsulfonyl moiety using a reducing agent, for example and without limitation, $SmI_2$; followed by an intramolecular coupling reaction, under conditions similar to those involved in the coupling of compound of Formula (I) with (II) in trivalent chromium, nickel and zinc. In an alternate method, the intramolecular coupling is performed in the presence of the chiral oxazole ligand, such as Ph-NMS-oxazole or sulfonamide to impart a higher yield and greater efficiency for the reaction. The subsequent oxidation using reagents as described above, can be performed to obtain compound of Formula (X).

Deprotection of the compound of Formula (X) can be performed using reagents known to a skilled person, for example, desilylation is performed using a fluoride source to give triol compound which is subjected to the intramolecular cyclization to result into the protected diol compound of Formula (XI). In one embodiment, for example and without limitation, the desilylation is performed using tetra-butyl ammonium fluoride (TBAF). In one embodiment, for example and without limitation, the intramolecular cyclization is performed using PPTS.

The deprotection of protected diol using suitable deprotecting agents such as PTSA results in the diol compound of Formula (XII).

Diol compound of Formula (XII) is useful intermediate for preparing various Halichondrin B analogs and particularly, eribulin or pharmaceutically acceptable salts thereof.

A selective protection of terminal alcohol of compound of Formula (XII) is carried out by converting the alcohol into a leaving group to form an intermediate compound followed by substitution of the leaving group by an amine or other nitrogen based nucleophile which results in eribulin.

In an embodiment, selective protection is carried out by using $Ts_2O$, TsCl, TMSOTf or MSCl in presence of a base such as collidine or lutidine.

In an embodiment, the amine or other nitrogen based nucleophile used is not limited to ammonia gas or a solution of ammonia in an organic solvent. In another embodiment, the nitrogen based nucleophile is an azide for example, trimethylsilyl azide ($TMSN_3$).

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents, ether solvents, protic solvents, aprotic solvents, hydrocarbon solvents and the like.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.). In some embodiments reaction may be performed below room temperature (below 22° C.) or under subzero temperature (below 0° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In a preferred embodiment compound (VII)-A is converted to eribulin as shown in Scheme E1

Scheme E1
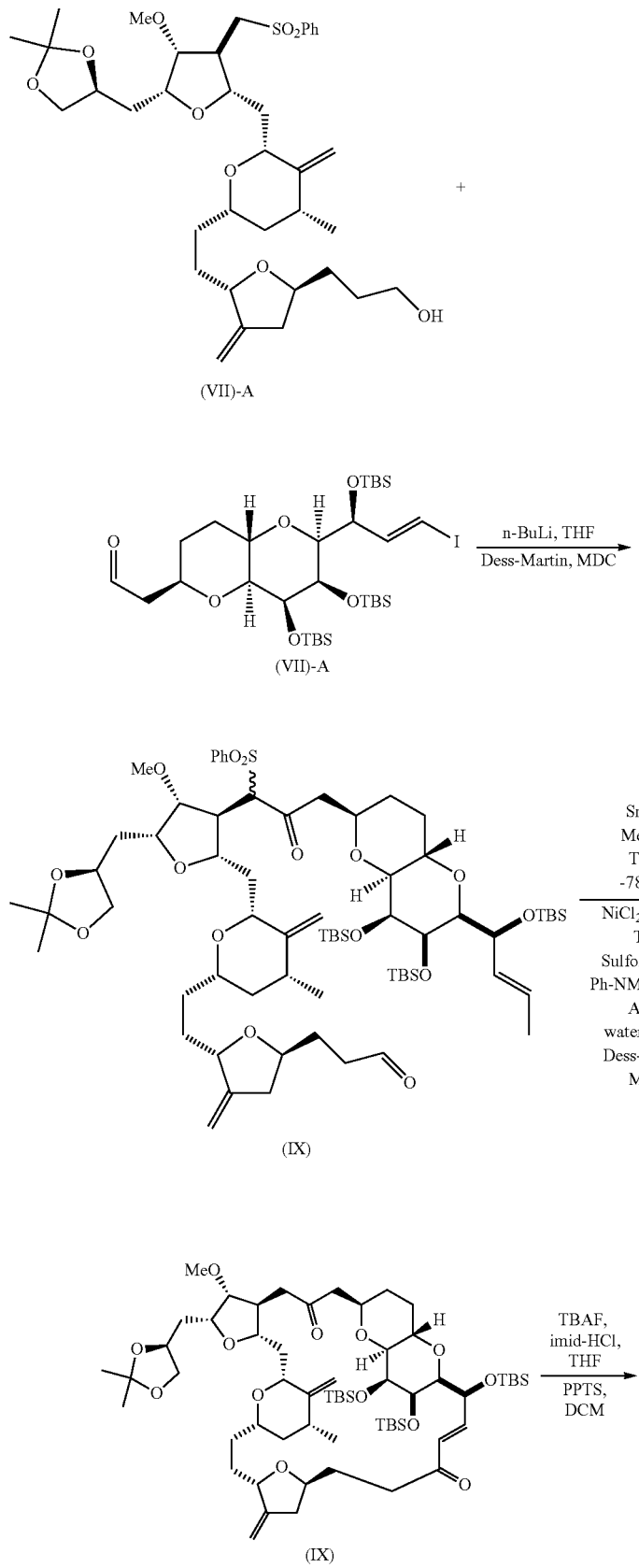

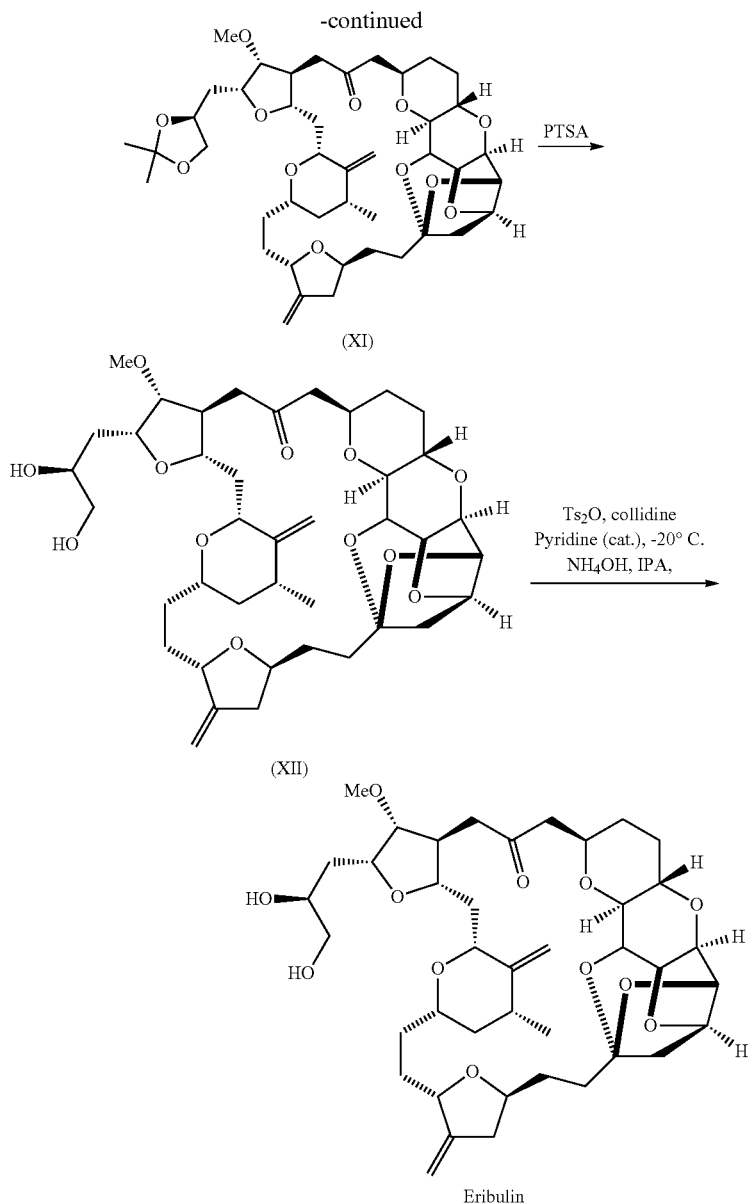

wherein R is methyl, $R_1$ and $R_2$ together form $CH_2SO_2Ph$, $PG_4$ and $PG_5$ together with the oxygen atoms to which they are attached, form a diol protecting 5 membered heterocyclic ring which is optionally substituted with methyl groups, $PG_8$, $PG_9$, $PG_{10}$ are TBS and X5 is iodo.

The compounds of Formula IX, X and XI are hitherto unreported intermediates useful in the process for the preparation of halichondrin B analogs as described herein.

Eribulin obtained by the process of the present invention may subsequently be converted to the corresponding pharmaceutically accepted salts by reacting with corresponding acid in suitable solvents.

The pharmaceutically acceptable salt of eribulin prepared according to the present invention, preferably having purity at least 98%, more preferably at least 99%, are selected from inorganic acid salt or organic acid salt. The inorganic acid salts may be selected from but not limited to hydrochloride, sulfate, hydrobromide, hydroiodide, nitrate, bisulfate and phosphate salts.

The organic acid salts may be selected from but not limited to ascorbate, malonate, citrate, cinnamate, malate, isonicotinate, acetate, lactate, salicilate, tartrate, pantotenate, ascorbate, succinate, stearate maleate, fumarate, gluconate, saccharate, formate, benzoate, glutamate, mesyalte, esylate, benzenesulfonate, p-toluenesulfonate, pamoate, lactate, oleate, tannate and oxalate salts. Preferably, eribulin is converted to mesylate salt.

While emphasis has been placed herein on the specific steps of the preferred process, it will be appreciated that many steps can be made and that many changes can be made in the preferred steps without departing from the principles of the invention. These and other changes in the preferred steps of the invention will be apparent to those skilled in the art from the disclosure herein, whereby it is to be distinctly understood that the foregoing descriptive matter is to be interpreted merely as illustrative of the invention and not as a limitation.

The details of the invention given in the examples which are provided below are for illustration only and therefore these examples should not be construed to limit the scope of the invention.

EXAMPLES

Example 1

Preparation of Compound (Ia)

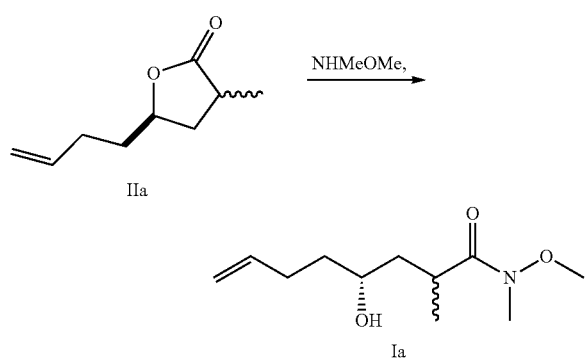

To a stirred solution of N, O-dimethyl hydroxyl amine hydrochloride (1.10 g, 0.011 mol) in DCM (20 ml), was added very slowly a solution of trimethyl alumina (2 M in toluene) (0.011 mol, 5.7 ml) at 0° C. under argon atmosphere and the reaction mass was allowed to stir at same temp for 10 min. Compound IIa (0.7 g, 0.004 mol) was taken in dry DCM (10 ml) and added slowly to the above reaction mixture. Reaction mass was stirred at RT for 5 hr. Reaction mass was quenched with 1.3 M disodium tartrate at 0° C., organic layer was extracted with ethyl acetate (3×50 ml), washed with water (10 ml) followed by brine (10 ml), dried over sodium sulphate and evaporated under reduced pressure to afford the compound Ia (0.4 g) which was used for the next step without any further purification.

Example 2

Preparation of Compound (Ib)

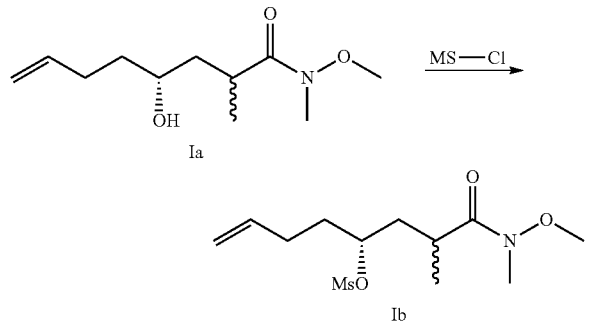

Compound Ia (0.4 g, Crude) was stirred in anhydrous THF (4 ml) and cooled to 0-5° C. Triethylamine (0.3 ml) was added followed by Methanesulfonyl Chloride (0.22 g). Stirred the reaction mass at 0-5° C. for 15 min. The reaction mixture was diluted with n-Heptane (100 ml). Organic layer was washed with brine (20 ml) solution and dried over sodium sulphate, evaporated under reduced pressure to give compound Ib (0.45 g) which was used in the next step without further purification.

Example 3

Preparation of Compound (Ic and Id)

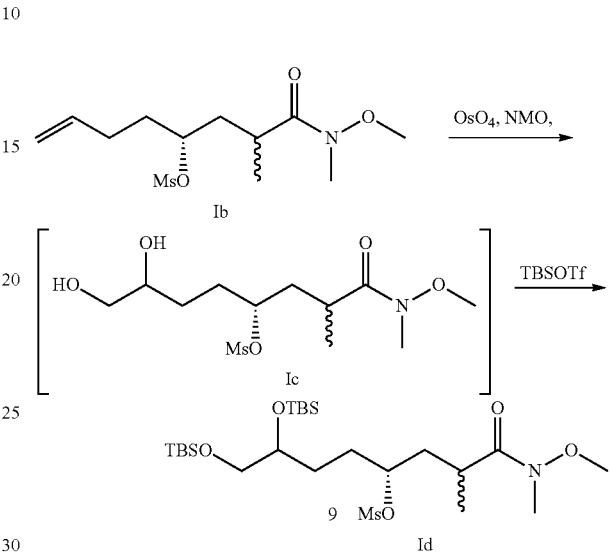

To a stirred solution of compound Ib (2 g, 6 mmol) in THF-H$_2$O (4:1, 26 ml) at 0° C. was added osmium tetroxide (4 ml, 1% t-BuOH solution) at 0° C. and stirred for 5 min, followed by addition of NMO(1.2g, 9.1 mmol) under nitrogen atmosphere, RM stirred for 1 h at RT. After completion of the reaction, the reaction mass was quenched with aq.Na$_2$SO$_3$ and extracted with 10% MeOH/DCM (2×50 ml), washed with water (25 ml) followed by brine (25 ml), dried over anhydrous sodium sulphate and evaporated under reduced pressure to obtain the compound Ic which was taken for the next step without further purification.

Compound Ic, was dissolved in 10 ml anhydrous THF and was treated with 2,6-lutidine (3.6 ml, 30.5 mmol) and TBSOTf (3.33 ml, 18.3 mmol) at 0° C. The reaction mass was allowed to warm to ambient temperature and stirred for 1 h. The reaction mass was quenched with MeOH (1 ml). The mixture was diluted with MTBE and the organic layer washed twice with saturated aqueous CuSO$_4$, dried over MgSO$_4$, filtered, and evaporated under reduced pressure to give crude compound Id. Crude compound Id was purified by column chromatography using SiO$_2$ and eluted with MTBE/hexanes mixture to give pure compound Id (yield 2 g, 80%).

Example 4

Preparation of Compound (Ie)

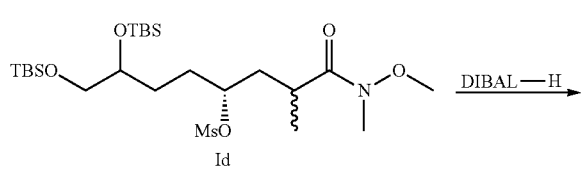

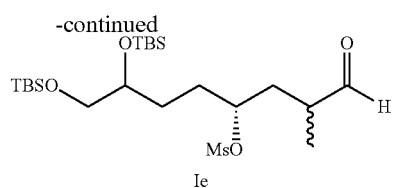

Ie

To a stirred solution of Id (2.0 g, 3.6 mmol) in anhydrous THF (80 ml) was treated with DIBAL-H (1.0 M in toluene, 3.6 ml at 0-5° C. slowly over 30 min and stirred the reaction mixture at same temperature for 1 h. Reaction mixture was quenched with MeOH (0.5 ml). MTBE (100 ml) was added followed by aqueous Rochelle's salt (50 ml), and stirred at room temperature for 30 min. The organic layer was separated, and the organic layer was washed with saturated aqueous Rochelle's salt (10 ml), water (20 ml), saturated NaHCO₃ (20 ml), and brine (20 ml). The organic layer was dried over MgSO₄, filtered, and concentrated to give Ie (Yield 1 g, 60%) as a colorless oil, which was taken onto the next step without further purification.

Example 5

Preparation of Compound (I)-A

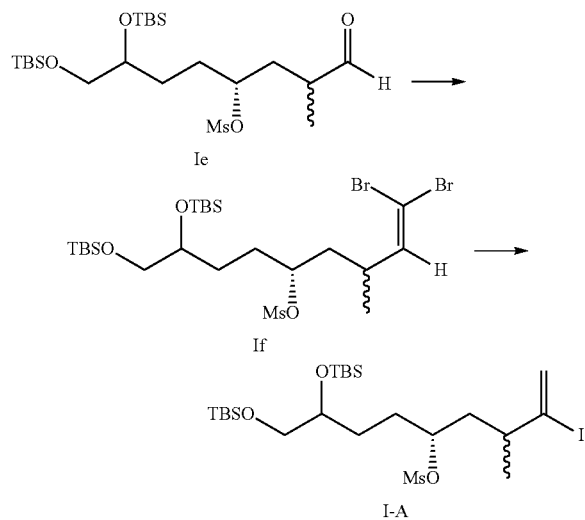

To a solution of triphenylphosphine (1.0 g, 8.0 mmol) in CH₂Cl₂ (20 ml) was added a solution of carbon tetrabromide (1.3 g, 4 mmol) in CH₂Cl₂ (10 ml) at 0-5° C. and the resultant suspension was stirred for 15 min. A solution of compound (Ie) (1 g, 2.0 mmol) in CH₂Cl₂ (2 ml) was added via syringe at 0-5° C. over 30 min. The reaction mixture was stirred at 10-15° C. for 1 h and then evaporated. The residue was passed through a short pad of silica gel and the solvent evaporated. The residue (1f) was taken for next step without purification.

To a stirred solution of (If) (1.1 g, 1.69 mmol) in anhydrous THF (20 ml) at −78° C. was added under nitrogen a solution of BuLi (1.6 M in hexane 2.1 ml, 3.38 mmol). The reaction mixture was further stirred at −78° C. for 1 h and then the temperature raised to 20-25° C. A 1.0M solution of Iodo-9-BBN in hexane (3.5 ml, 3.5 mmol) was added. After being stirred at room temperature for 2 h, the reaction mixture was quenched with saturated aqueous NH₄Cl solution and extracted with MTBE (3×50 ml). The combined organic layers were washed with brine (20 ml), dried over anhydrous Na₂SO₄, and evaporated under reduced pressure. Crude compound I-A was purified by column chromatography using SiO₂ and eluted with a mixture of MTBE: Hexane to give pure compound I-A (Yield 550 mg, 52%).

Example 6

Preparation of Compound (II)

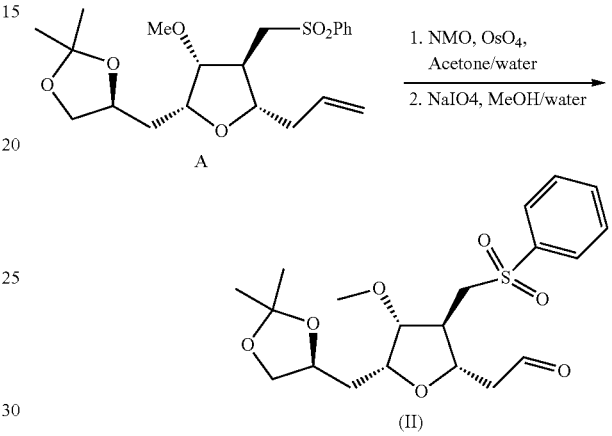

Compound (A) (500 mg, 1 eq) was dissolved in Acetone (10 Vol) and DM water (8 Vol). The reaction mixture was cooled to 10-15° C. Then Charged NMO (0.214 g, 1.5 eq) in one portion into the reaction mass and stirred for 15 min. OsO4 (4% solution in water) (0.01 eq) was added drop wise by keeping internal temp below 20° C. The temperature was raised to 20-25° C. and stirred for 2 hrs. Reaction was monitored by TLC (10% Ethyl acetate in Hexane, KMnO₄ active). Poured the reaction mass into 10% sodium bisulphite solution (15 Vol) and extracted with Ethyl acetate (3×5 Vol). The combined organic layers were washed with brine solution (5 Vol), dried over Na₂SO₄ and evaporated under reduced pressure below 45° C. to get 300 mg Di-ol intermediate.

Di-ol intermediate (300 mg) was dissolved in Methanol (3.0 ml, 10.0 Vol) and DM water (1.2 ml, 4.0 Vol) at 20-25° C. NaIO4 (0.296 g, 2.0 eq) was charged in one portion into the reaction mass at 20-25° C. and stirred for 1 hr at the same temp. Reaction was monitored by TLC (10% Ethyl acetate in Hexane, KMnO₄ active). Reaction mass was quenched with water (10 Vol) and extracted with Chloroform (3×8 Vol). The combined organic layer was washed with brine solution (5 Vol), dried (Na₂SO₄) and evaporated under reduced pressure below 45° C. to get the crude compound-(II). The crude compound was purified by column chromatography over silica gel (100-200 mesh) by eluting with 5-40% Ethyl acetate in Hexane. Desired fraction was concentrated to afford 150 mg (30%) of pure compound (II).

Example 7

Preparation of Compound (III b)

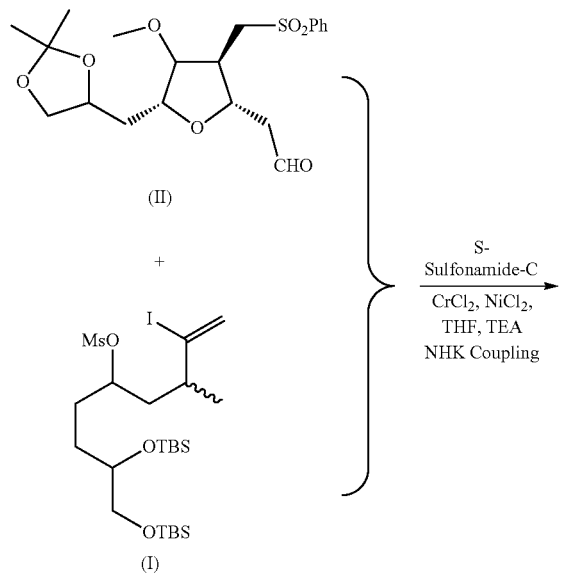

Sulfonamide-C (53.0 mg, 0.22 eq) was weighed outside a glove box and put in a flask. In a glove box, proton sponge (30 mg, 0.22 eq), CrCl$_2$ (12 mg, 0.20 eq) and MeCN (1.5 ml) were added and the resulting mass was then stirred at 25-30° C. for 1 h. The resulting solution was added to a reaction vial containing mixture of compound (II) (200 mg, 1 eq), compound (I) (506 mg, 1.5 eq), LiCl (41 mg, 2.0 eq), Mn powder (53 mg, 2.0 eq), Zr(Cp)$_2$Cl$_2$ (212 mg, 1.5 eq) and NiCl$_2$.dmp (3.1 mg, 0.05 eq). The resulting mass was stirred at 25-30° C. in the glove box for 6 h. The reaction mixture was diluted with ethyl acetate (10 ml), and treated with florisil (0.5 g). The resulting suspension was stirred for 1 h at 25-30° C. and then passed through a short pad of silica gel. The solvent evaporated and the compound (IIIa) was taken for next step without purification.

Compound (IIIa) was stirred in anhydrous THF (106 ml) under argon atmosphere and cooled the reaction mixture to −15-20° C., Then a solution of 0.5 M KHMDS in toluene (2 ml) was added at rate such that internal temperature did not exceed −12° C. Reaction mixture was quenched with saturated ammonium chloride solution below 0° C. MTBE was added, stirred for 5-10 min and the layers separated. Combined all the organic layers and washed with saturated ammonium chloride solution (10 ml) followed by brine solution (10 ml) and dried over sodium sulphate and evaporated under reduced pressure. The product was purified by column chromatography by using SiO$_2$ by eluting with Hexane/MTBE mixture. The fractions collected and evaporated to give (IIIb) (Yield 170 mg, 43%).

Example 8

Preparation of Compound (IIIc)

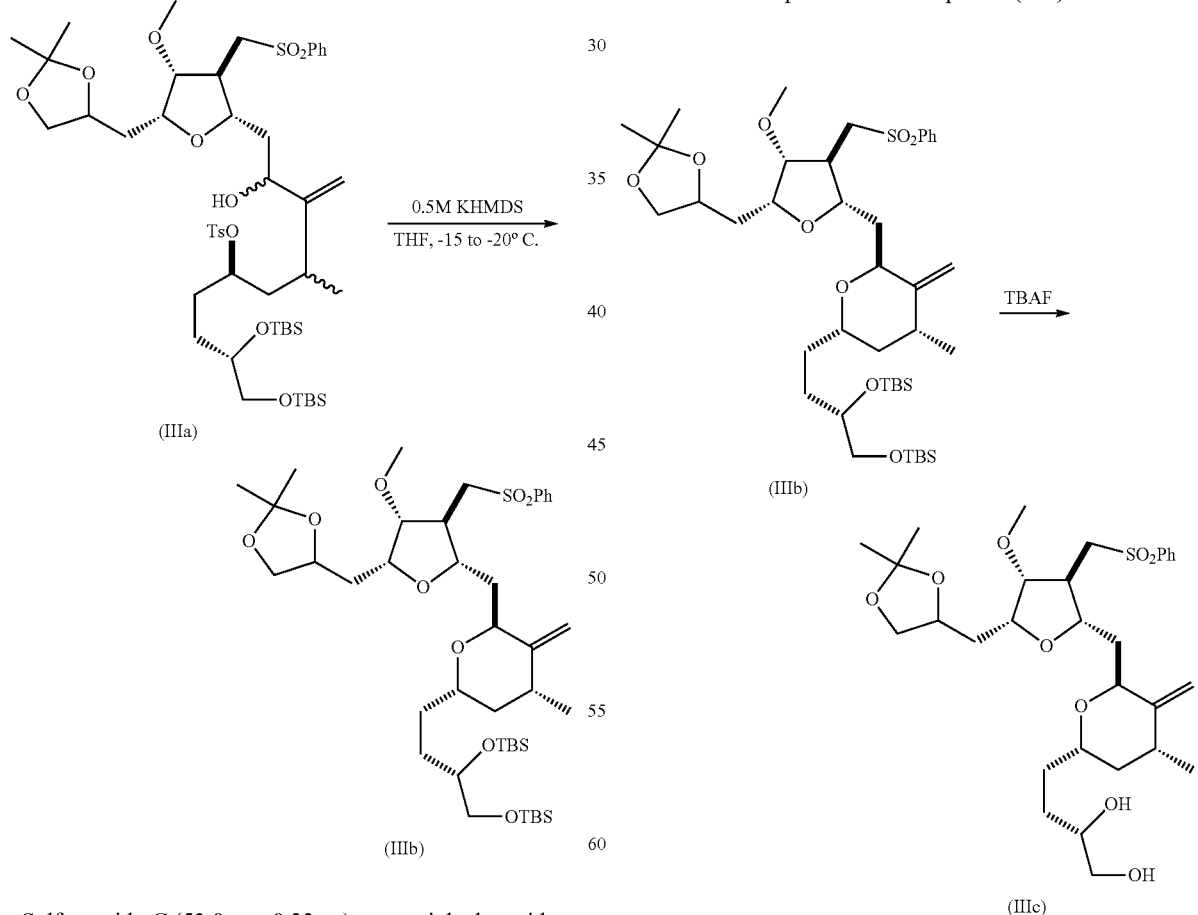

To a stirred solution of (0.15 g, 0.18 mmol) compound (III b) in anhydrous THF (20 ml), was added slowly a solution of tetrabutylammonium fluoride (0.7 ml, 0.7 mmol) (1.0 M solution in THF) at 0-5° C. under argon atmosphere. Reaction mass was allowed to stir at room temperature for 1 hour and the disappearance of the target compound was checked by TLC. The reaction mass was concentrated and the residue was purified by SiO₂ column chromatography using Hexane/MTBE, respective fractions were evaporated to give (IIIc) (Yield 70 mg, 70%).

Example 9

Preparation of Compound (III)-A

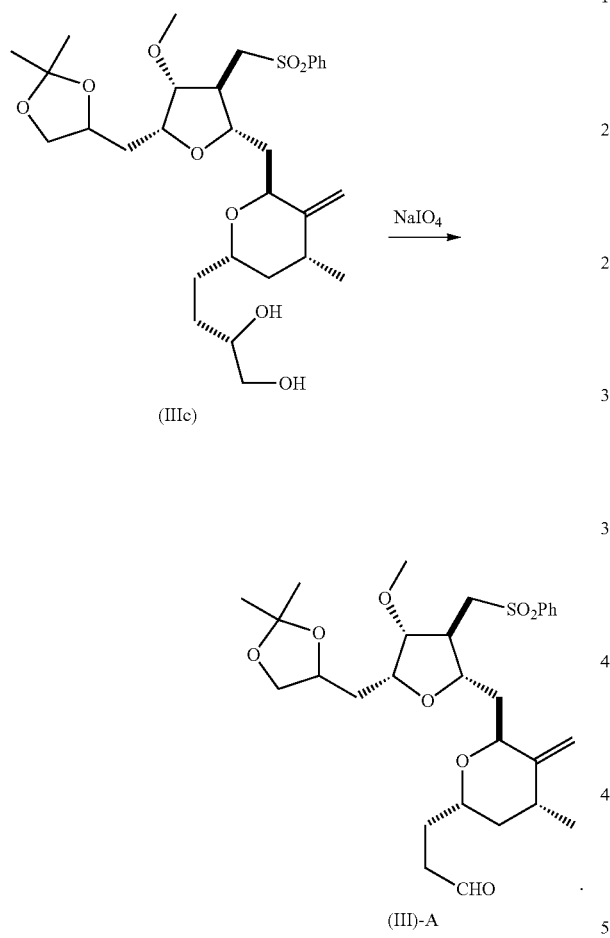

Compound (IIIc) (0.1 g, 0.17 mmol) was dissolved in a mixture of ethyl acetate (2 ml) and water (2 ml). NaIO₄ (0.04 g, 0.19 mmol) was added portion wise over 1 hour at 0-5° C. The reaction mass was further stirred at 0-5° C. for 1 hour. The reaction mixture was treated with NaCl solid (1 g) at 0-5° C. and further stirred at same temperature for 30 min. The reaction mixture was filtered and the cake was washed with ethyl acetate (10 ml). Separated the organic layer, aqueous layer was extracted with ethyl acetate (3×5 ml). The combined organic layers were washed with brine solution (5 ml). The organic layer was concentrated and the residue was stripped off with toluene (20 ml) and DCM (20 ml) and used for the next step without further purification.

Example 10

Preparation of Compound (V)-A

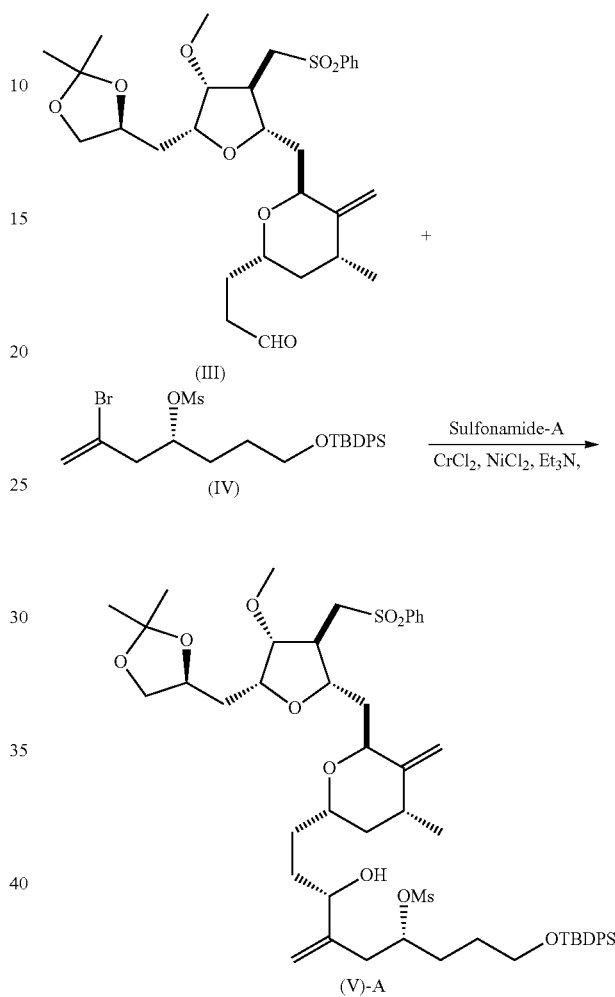

Anhydrous chromous chloride (200 mg, 1.62 mmol) was taken in clean dry RBF under argon atmosphere in glove box. Sulfonamide A (500 mg, 1.62 mmol) was dissolved in dry THF (20 ml) and added to it followed by triethyl amine (0.23 ml, 1.62 mmol). The resulting light green solution was heated at 40° C. for 1 hr and then cooled to 0° C. NiCl₂ (23mg, 0.695 mmol) was added to the reaction mass under argon atmosphere followed by the addition of compound (IV) (91 mg, 0.43 mmol) and compound (III) (200 mg, 0.36 mmol) in dry THF(2 ml). The reaction mass was allowed to stir at RT for 16 h, the reaction mass was diluted with THF (5 ml) and filtered over celite pad. The filtrate was concentrated under reduced pressure to obtain the compound (V)-A which was used in the next step without any further purification.

Example 11

Preparation of Compound (VI)

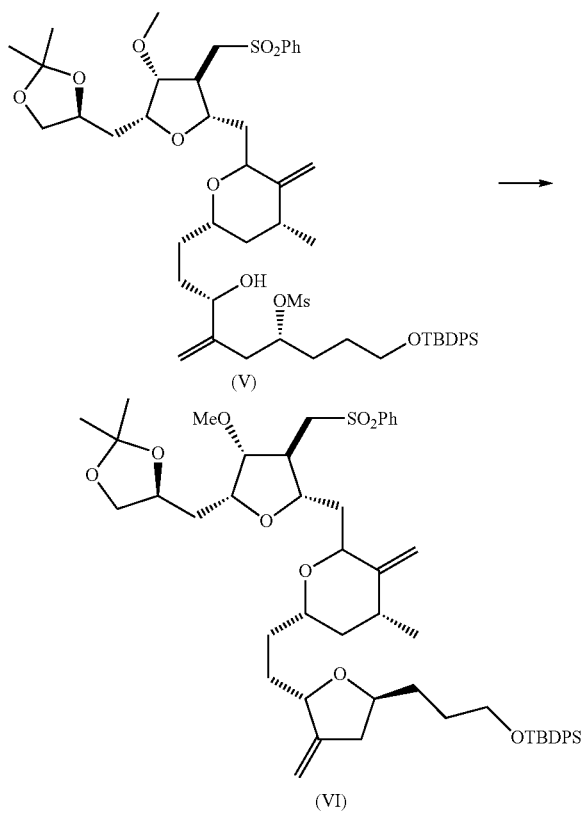

To a stirred solution of crude compound (V)-A in Isopropyl Alcohol (3 ml), was added pyridine (0.15 ml) and PPTS (50 mg) and the reaction mass was stirred at room temperature under argon atmosphere for 16 hr. The reaction mass was evaporated under reduced pressure to afford the crude compound which was purified via column chromatography using 230-400 silica gel eluting with MTBE: Hexane mixture to afford compound (VI) (Yield 100 mg, 0.31%)

Example 12

Preparation of Compound (VII)-A

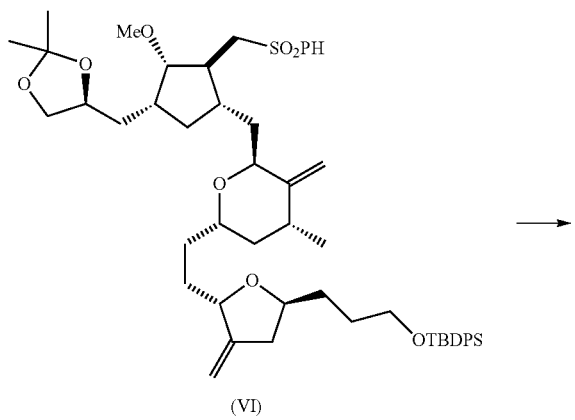

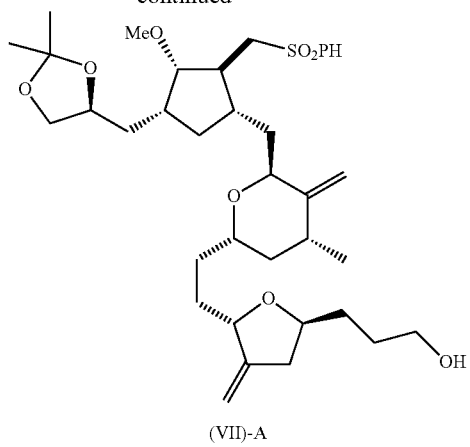

Compound (VI) (150 mg, 0.166 mmol) was dissolved in anhydrous tetrahydrofuran (5 ml), at room temperature under nitrogen atmosphere. Tetrabutylammonium fluoride (1M in THF) (0.25 ml, 0.25 mmol) was added at 0-5° C. over 30 min. The reaction mixture was stirred at room temperature for 16 hours. The reaction was quenched with saturated aqueous ammonium chloride solution (5 ml) and the mixture was extracted with MTBE (3×15 ml). The combined organic layers were dried over sodium sulphate, and evaporated under reduced pressure to give crude compound of (VII)-A. Crude was purified by column chromatography using MTBE: Hexane mixture as an eluent. The compound (VII)-A was afforded as a white foam (Yield 80 mg, 80%).

Example 13

Preparation of Compound (IX)

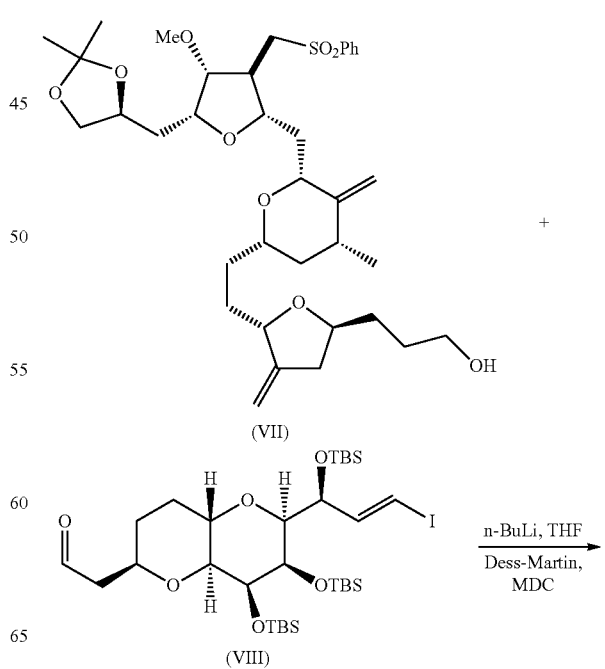

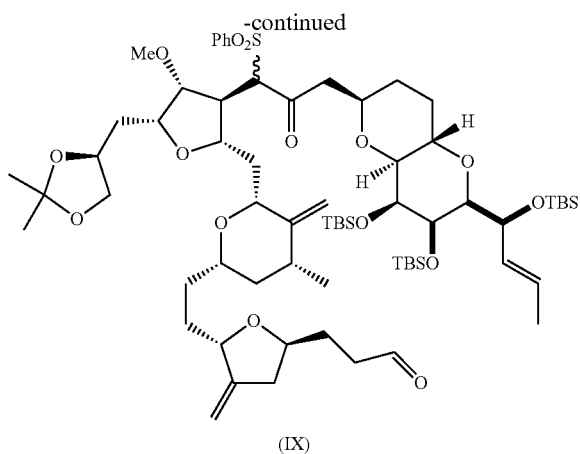

(IX)

Compound (VII) (50 mg, 0.075 mmol) was stirred in anhydrous tetrahydrofuran (2.5 ml) cooled to −75° C., and treated with n-butyl lithium (1.6M in hexane) of (0.24 ml) at same temperature and stirred for 30 min. A solution of Compound (VIII) (68 mg, 0.092 mmol) in n-hexane (3 ml) was added slowly at −75° C. over 10 min. The reaction mixture was stirred at −70 to −75° C. for 30 min. The reaction mixture was quenched with saturated ammonium chloride (5 ml) and diluted with MTBE (15 ml) and water (5 ml). The organic layer was separated and dried over sodium sulphate, evaporated under reduced pressure to get crude compound. Crude was purified by column chromatography to give Hydroxy compound (Yield 75 mg, 71%) which was taken for the next step.

Hydroxy compound (75 mg, 0.05 mmol) was dissolved in dichloromethane (2 ml, moisture content ~400 ppm) at rt. Dess-Martin (50 mg, 0.125 mmol) was added in one portion at 20-25° C. and stirred for 10 min. The reaction mixture was quenched with saturated sodium bicarbonate (2 ml) and 10% aqueous sodium sulfite (2 ml) and stirred for 30 minutes. The mixture was diluted with saturated sodium chloride (5 ml) and extracted with MTBE (2×15 ml). The aqueous layer was discarded and the organic layer concentrated and purified by silica gel chromatography to afford compound (IX) (Yield 55 mg, 73%). The material was stored under inert gas atmosphere at −20° C.

Example 14

Preparation of Compound (X)

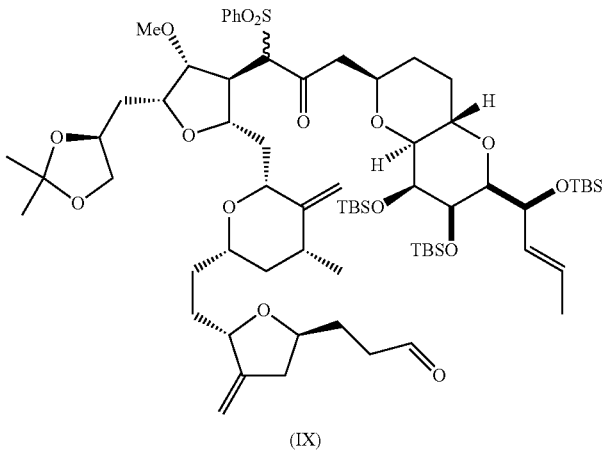

(IX)

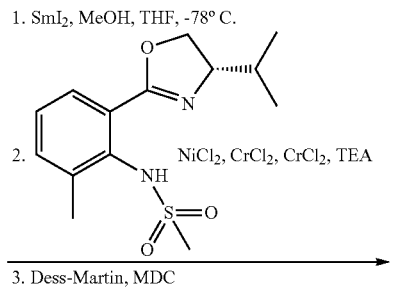

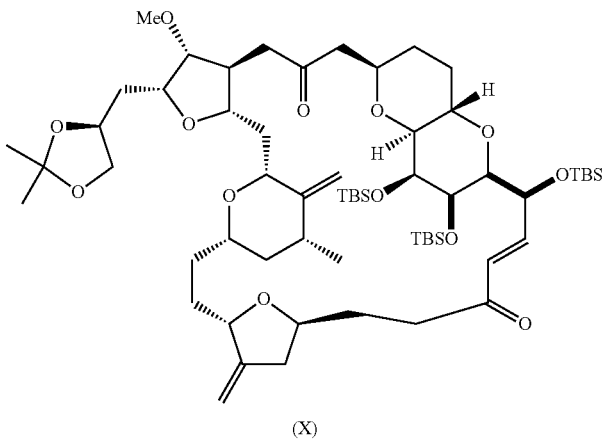

(X)

Samarium di-iodide solution (0.089 ml, 0.089 mmol) was taken in a pre-dried RBF under argon atmosphere and the solution cooled to internal temperature −70° C. Compound (IX) (50 mg, 0.035 mmol) was dissolved in a mixture of anhydrous methanol (0.5 ml) and anhydrous THF (0.5 ml) and cooled to −70° C. Compound (IX) was added to the cold samarium solution at a rate such that the internal temperature did not exceed −70° C. The reaction was quenched with potassium carbonate/Rochelle's Salts/water (1/10/100; w/w/v, 5 ml) and MTBE (15 ml) such that internal temperature did not exceed −65° C. Upon complete addition of the workup solution, the reaction was warmed to room temperature. The organic layer was separated, evaporated under reduced pressure. Crude was purified by column chromatography to afford de-sulfonyl compound (Keto-aldehyde) (Yield 25 mg, 55%). The material was stored under inert gas atmosphere at −20° C.

Sulfonamide-B (42 mg, 0.14 mmol) was weighed in a glove box under argon atmosphere. The CrCl$_2$ (37 mg, 0.3 mmol) was added in one portion followed by anhydrous acetonitrile (2 ml) and the mixture was warmed and maintained temperature between 30-35° C. Triethylamine (0.043 ml, 0.3 mmol) was added in one portion and the mixture stirred for 1 h. The NiCl$_2$ (4 mg, 0.03 mmol) was added in one portion, followed by a solution of keto-aldehyde (50 mg, 0.03 mmol) in anhydrous THF (1.5 ml) over 30 minutes. The warm was removed, then heptane (20 ml) and Celite (0.5 g) were added. The mixture was stirred for 5 minutes and filtered over a pad of Celite (1.5 g) and the Celite pad rinsed with heptane (20 ml) and acetonitrile (3 ml). Separated the heptane layers, combined and washed with acetonitrile (5 ml). The heptane layer was evaporated under reduced pressure and the product purified by silica gel chromatography to afford Cyclized-Hydroxy compound (Yield 28 mg, 68%).

Cyclized-Hydroxy compound (50 mg, 0.044 mmol) was dissolved in dichloromethane (3 ml, moisture content ~400 ppm) at rt. Dess-Martin (28 mg, 0.066 mmol) was added, stirred for 10 min at rt. The reaction mixture was quenched with saturated sodium bicarbonate (3 ml) and 10% aqueous sodium sulfite (3 ml) and stirred for 30 minutes. The mixture was diluted with saturated sodium chloride (5 ml) and extracted with DCM (2×15 ml). The aqueous layer was discarded and the organic layer concentrated and purified by, silica gel chromatography to afford compound (X) (Yield 35 mg, 73%). The material was stored under inert gas atmosphere at −20° C.

Example 15

Preparation of Compound (XI)

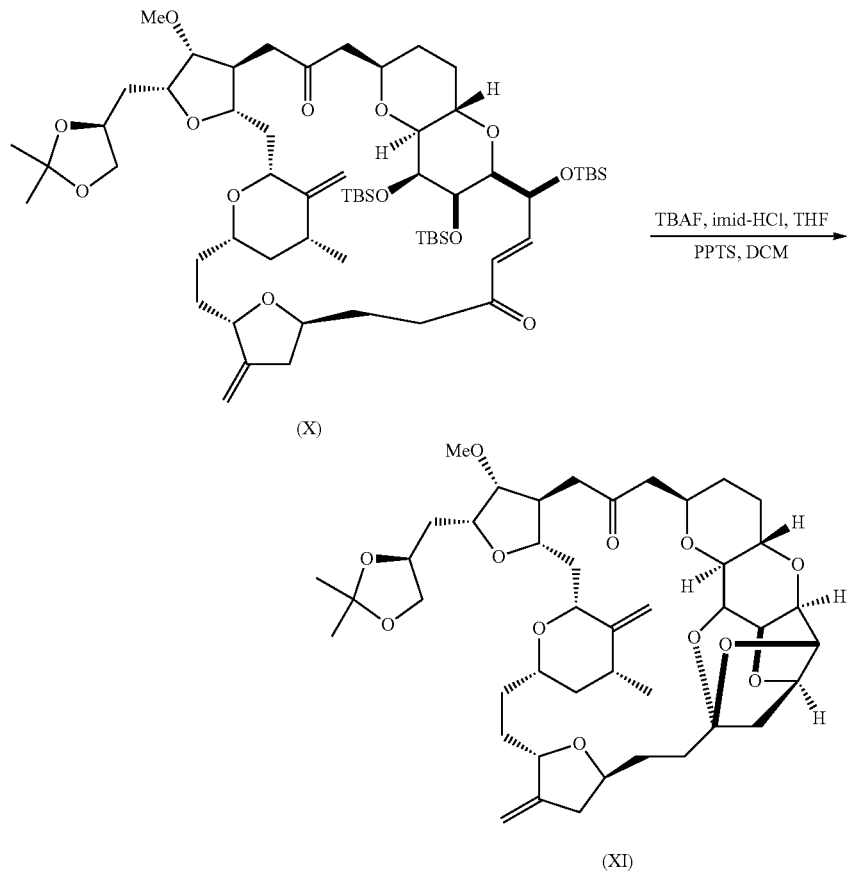

To a solution of imidazole hydrochloride (60 mg, 0.56 mmol), 1 M TBAF in THF (1.4 ml, 1.4 mmol) was taken in anhydrous THF (0.5 ml) at ambient temperature under nitrogen atmosphere, The resulting mixture was stirred for 20-30 min until it is homogenous. Into another RBF, compound (X) (80 mg, 0.07 mmol) was taken in anhydrous THF (4 ml) and stirred for 10-15 min until compound dissolve completely. The TBAF/Imidazole mixture was charged as single portion into the reaction mixture and stirred at rt for 3-4 days. Crude was purified by silica gel chromatography to afford pure TBS de-protected compound.

TBS de-protected compound was dissolved in anhydrous dichloromethane (4 ml) under a nitrogen atmosphere and treated with PPTS (105 mg, 0.42 mmol). After 40-60 minutes, the reaction mixture was directly purified by column chromatography. Collected all the fractions and evaporated under reduced pressure, strip off toluene (2×10 ml) to give compound (XI) (Yield 26 mg, 46%).

Example 16

Preparation of Compound (XII)

To a solution of compound (XI) (50 mg, 0.06 mmol) in a mixture of isopropyl acetate (3 ml) and propionic acid (1 ml), after the addition of water (0.5 ml), was added at 0-5° C. p-toluene sulfonic acid (3 mg, cat amount) in 0.1 ml in water under nitrogen atmosphere. Then, the reaction mixture was stirred at room temperature for 3 h. After complete conversion of (XI) diluted the reaction mixture with isopropyl acetate (15 ml) and washed with water (2×5 ml) and brine solution (5 ml). The organic layer was dried over sodium sulphate and evaporated under reduced pressure to afford the crude compound (XII) which was used for the next step without any further purification.

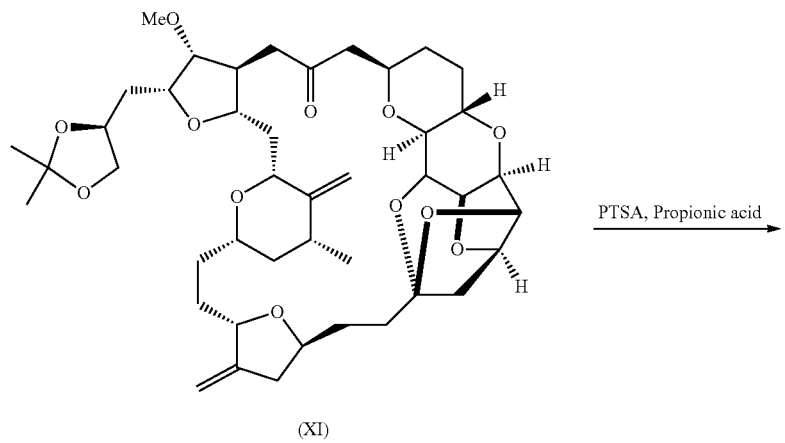

Example 17

Preparation of Eribulin

Preparation of Eribulin is carried out by the method reported in the art.

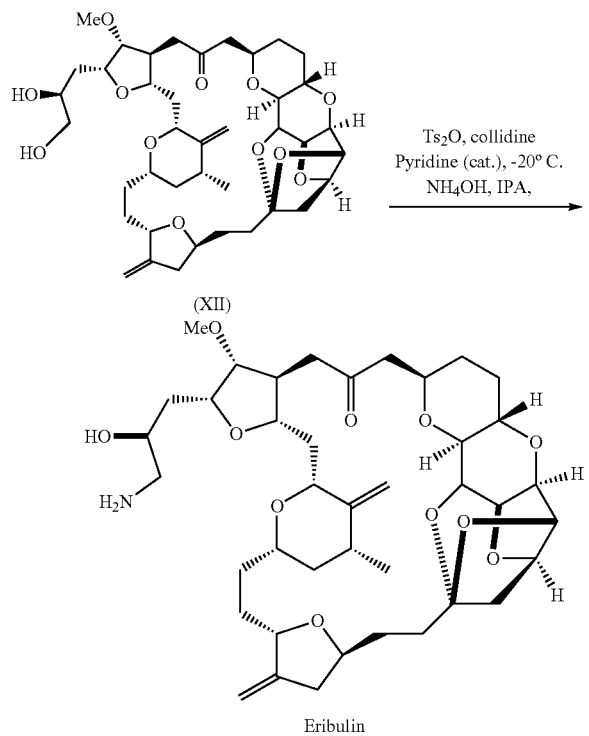

Accordingly, Compound (XII) (40 mg, 0.05 mmol) was stripped off with anhydrous toluene (2×3 ml) and then diluted with anhydrous DCM (3 ml) under argon atmosphere. Collidine (0.054 ml, 0.4mmol) was added, followed by anhydrous DCM containing catalytic amount of pyridine (1.5 ml). The resulting mixture was cooled to an internal temperature of −20 to −25° C. p-Toluenesulfonic anhydride (18 mg, 0.055 mmol) in anhydrous DCM (0.5 ml) under argon atmosphere was added slowly maintaining internal temperature below −16° C. The reaction was stirred at −20 to −25° C. for 90 minutes then warmed to 0° C. over 20 minutes and stirred for an additional 30 minutes. The reaction mixture was quenched with water (2 ml). The bath was removed and reaction mixture was allowed to warm to room temperature and stirred for 30 min. The reaction mixture was transferred to another flask containing IPA (20 ml) and aqueous ammonium hydroxide (20 ml) at room temperature, stirred for 24 hours. The reaction was concentrated to dryness or near dryness at reduced pressure. The resulting material was diluted with DCM (20 ml) and washed pH 10 buffer (NaHCO$_3$/Na$_2$CO$_3$ (aq), 20 ml). The aqueous phase was back extracted with DCM (2×25 ml) and the combined organic layers were concentrated to dryness. The resulting free amine (eribulin crude) was purified by Reverse phase column chromatography. The pooled fractions were evaporated under reduced pressure below 30° C. and lyophilized the material to afford Eribulin (Yield 26 mg, 65%).

We claim:

1. A process for the preparation of a compound of formula I

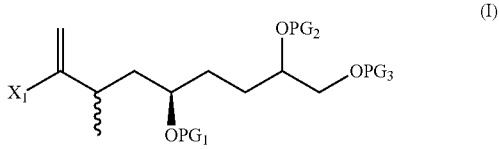

comprising:

(i) reacting a compound of Formula (Ia)

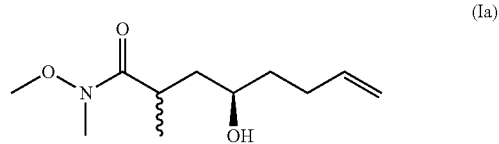

with a first protecting agent in the presence of a base to obtain a compound of Formula (Ib)

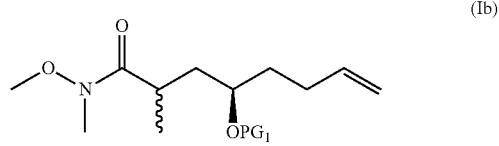

(ii) reacting the compound of Formula (Ib) with a hydroxylating agent to form a vicinal diol of Formula (Ic)

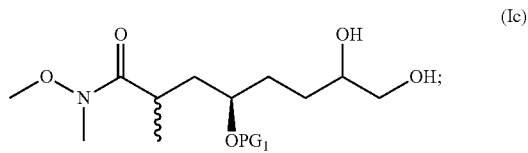

(iii) protecting the vicinal diol of Formula (Ic) with a second protecting agent to form a compound of Formula (Id):

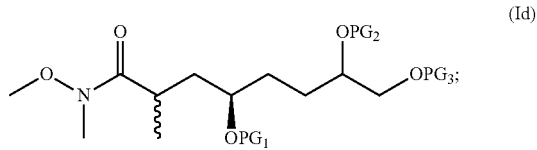

(iv) reducing the compound of Formula (Id) with a reducing agent to form a compound of Formula (Ie):

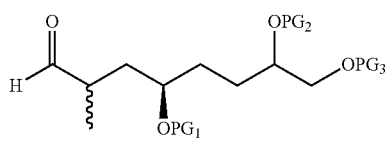

(v) reacting the compound of Formula (Ie) with a halogenating agent to form a compound of Formula (If):

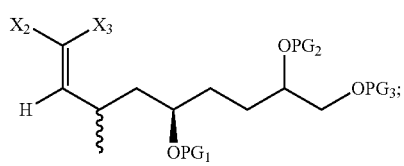

and (vi) alkynation and haloboration of the compound of Formula (If) to form the compound of Formula (I);
wherein $PG_1$, $PG_2$ and $PG_3$ are independently hydrogen or hydroxyl protecting groups; and
$X_1$, $X_2$ and $X_3$ are leaving groups.

2. The process of claim 1, further comprising preparing the compound of Formula (Ia) by reacting a compound of Formula (IIa)

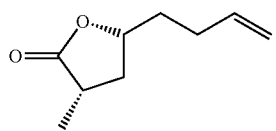

with dimethyl hydroxyl amine.

3. The process of claim 1, wherein the compound of formula I is a compound of formula (I-A)

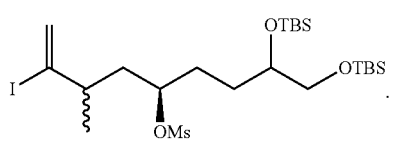

4. A process for the preparation of a compound of formula III

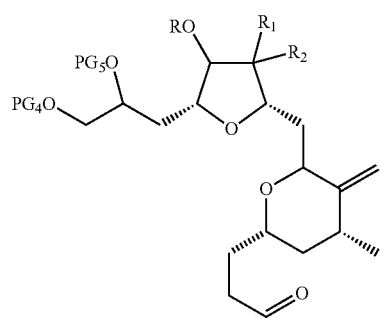

which comprises:

preparing a compound of formula I according to the process of claim 1;

converting the compound of formula I into the compound of formula III;

wherein $PG_1$, $PG_2$, $PG_3$, are as defined in claim 1; and $PG_4$ and $PG_5$ are independently H or C1-6 alkyl; or $PG_4$ and $PG_5$, together with the oxygen atoms to which they are attached, form a diol protecting 5- to 6-membered heterocyclic ring, which is optionally substituted with C1-4 alkyl groups;

$R_1$ and $R_2$ are each independently selected from the group consisting of H, and —$CH_2SO_2Ar$; or $R_1$ and $R_2$ together form =$CH_2SO_2Ar$, Ar is an aryl group; and R is H, C1-6 alkyl or C1-6 haloalkyl.

5. The process according to claim 4, wherein said conversion comprises:

(i) intramolecular coupling of a compound of Formula (I) with a compound of Formula (II)

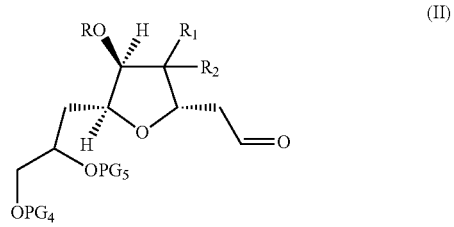

to form a compound of Formula(IIIa):

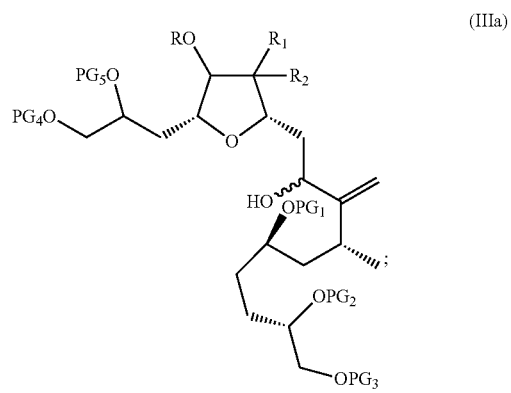

(ii) intramolecular cyclization of the compound of Formula(IIIa) to form a compound of Formula (IIIb):

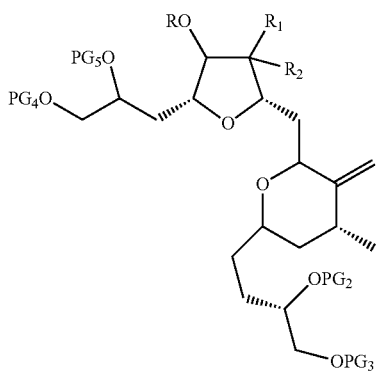

(IIIb)

(iii) deprotection of the compound of Formula(IIIb) to form a compound of Formula (IIIc):

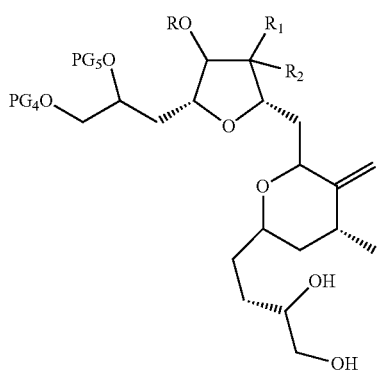

(IIIc)

and (iv) reducing the compound of Formula (IIIc) with a reducing agent to form the compound of Formula (III).

6. The process according to claim 4, wherein the compound of formula III is a compound of formula (III-A)

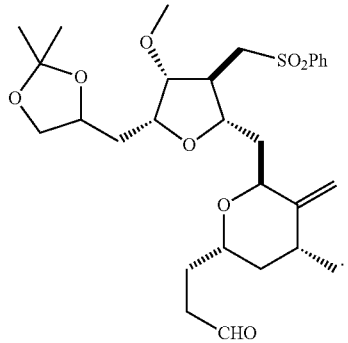

(III)-A

7. A process for the preparation of compound of formula V

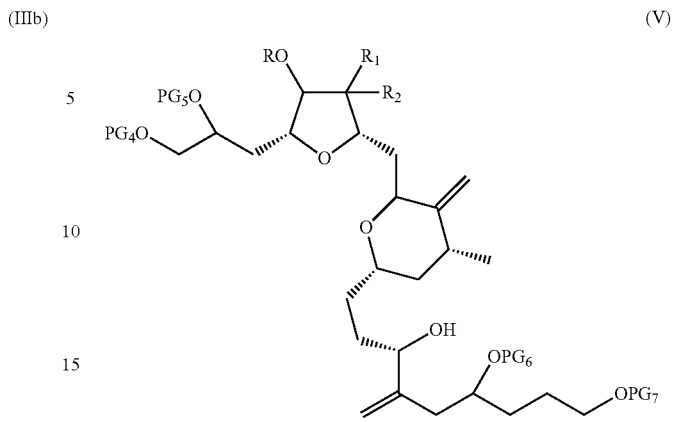

(V)

which comprises:

preparing a compound of formula III according to the process of claim 4; and converting the compound of formula III into the compound of formula V;

wherein $PG_4$, $PG_5$, R, $R_1$ and $R_2$ are as defined in claim 4, and each of $PG_6$ and $PG_7$ are independently hydrogen or a hydroxyl protecting group.

8. The process according to claim 7, wherein said conversion comprises:

intramolecular coupling of the compound of Formula (III) with a compound of Formula (IV)

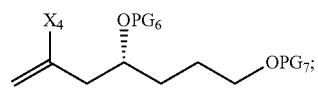

(IV)

wherein $PG_6$ and $PG_7$ are independently H or C1-6 alkyl; and $X_4$ is a leaving group.

9. The process according to claim 7, wherein the compound of formula V is a compound of formula (V-A)

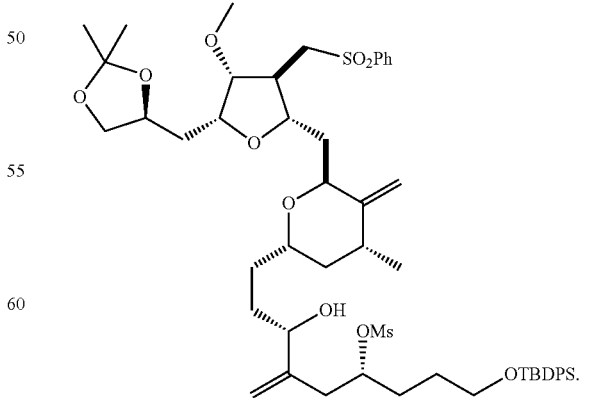

(V)-A

10. A process for the preparation of a compound of formula VII (VII)

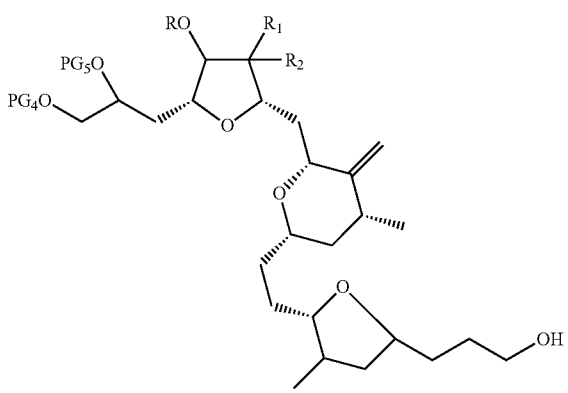

which comprises:
preparing a compound of formula V according to the process of claim 7; and
converting the compound of formula V into the compound of formula VII.

11. The process according to claim 10, wherein said conversion comprises steps of:
(i) intramolecular cyclization of the compound of Formula (V) to form a compound of Formula (VI):

(VI)

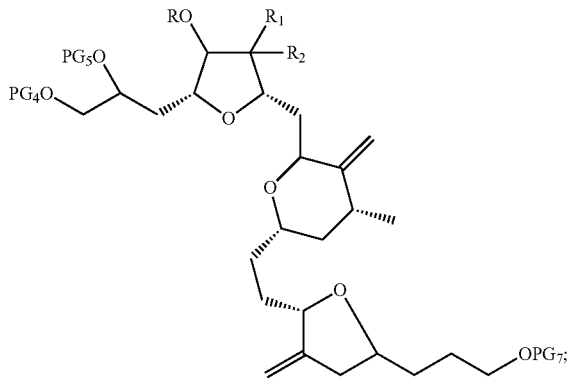

and
(ii) deprotecting the compound of Formula (VI) to form the compound of Formula (VII).

12. The process according to claim 10, wherein the compound of formula VII is a compound of formula (VII-A)

(VII)-A

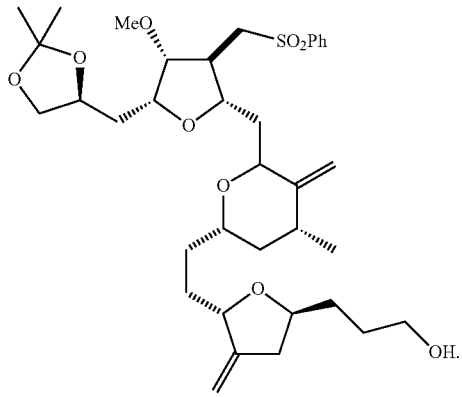

13. A process for preparing eribulin, or a pharmaceutically acceptable salt thereof, said process comprising the steps of:

(a) producing a compound of Formula (VII) by the method of claim 10; and
(b) converting the compound of Formula (VII) into eribulin, or a pharmaceutically acceptable salt thereof.

14. A process for preparing eribulin, or a pharmaceutically acceptable salt thereof, said process comprising the steps of:
(a) producing a compound of Formula (VII-A) by the method of claim 12;
(b) converting the compound of Formula (VII-A) into eribulin, or a pharmaceutically acceptable salt thereof.

15. A process for preparing a pharmaceutical composition containing eribulin or a pharmaceutically acceptable salt thereof, comprising:
preparing eribulin or a pharmaceutically acceptable salt thereof in accordance with a process of claim 13; and
converting the eribulin or the pharmaceutically acceptable salt thereof into the pharmaceutical composition.

16. A process for preparing a pharmaceutical composition containing eribulin or a pharmaceutically acceptable salt thereof, comprising:
preparing eribulin or a pharmaceutically acceptable salt thereof in accordance with a process of claim 14; and
converting the eribulin or the pharmaceutically acceptable salt thereof into the pharmaceutical composition.

17. An intermediate useful in the preparation of eribulin, selected from the group consisting of:
a compound of formula (I);

(I)

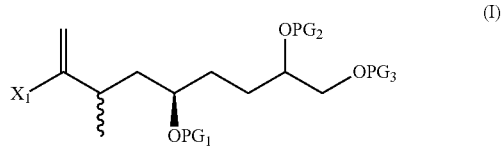

a compound of formula (I-A):

(I)-A

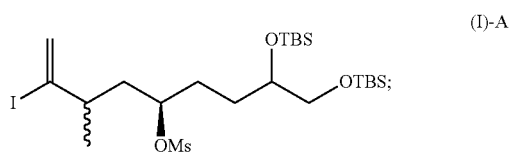 [SMILES: C=C(I)C(C)C[C@@H](CCC(CO[Si](C)(C)C(C)(C)C)O[Si](C)(C)C(C)(C)C)OS(C)(=O)=O]

a compound of formula (V):

(V)

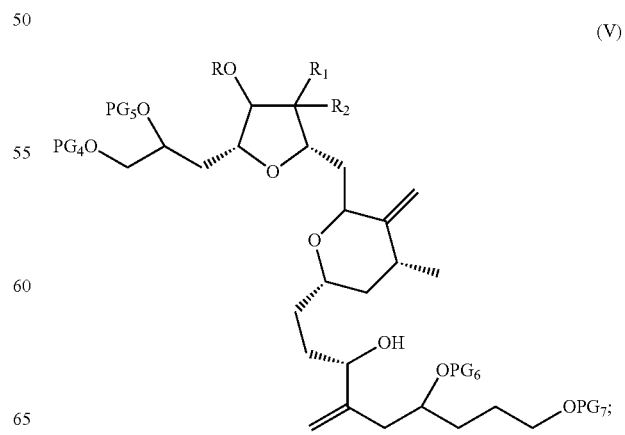

a compound of formula (V-A):

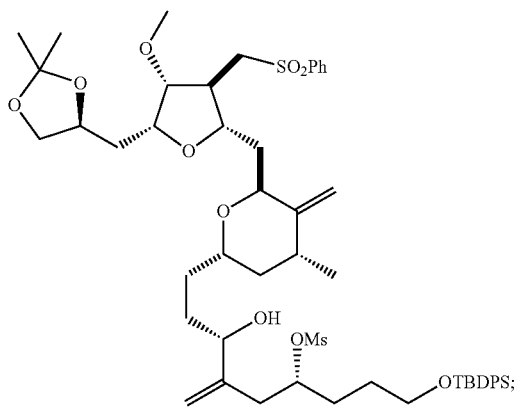
(V)-A and wherein $PG_1$, $PG_2$, $PG_3$, $PG_4$, $PG_5$, $PG_6$, and $PG_7$ are independently hydrogen or hydroxyl protecting groups;

$X_1$ is a leaving group; and $R_1$ and $R_2$ are each independently selected from the group consisting of H, and —$CH_2SO_2Ar$; or $R_1$ and $R_2$ together form =$CH_2SO_2Ar$, where Ar is an aryl group; and R is H, C1-6 alkyl or C1-6 haloalkyl.

18. An intermediate useful in the preparation of eribulin, selected from the group consisting of:

a compound of formula (I); and

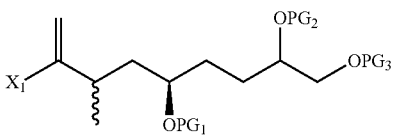
(I)

a compound of formula (I-A):

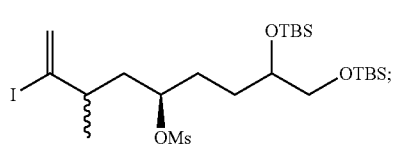
(I)-A wherein $PG_1$, $PG_2$, and $PG_3$ are independently hydrogen or hydroxyl protecting groups;

$X_1$ is a leaving group.

19. The intermediate of claim 18, wherein the intermediate is a compound of formula (I).

* * * * *